(12) United States Patent
Joseph et al.

(10) Patent No.: US 9,901,622 B2
(45) Date of Patent: Feb. 27, 2018

(54) RAPID ACTION INSULIN FORMULATIONS AND PHARMACEUTICAL DELIVERY SYSTEMS

(71) Applicant: Thermalin Diabetes, LLC, Waban, MA (US)

(72) Inventors: Jeffrey I. Joseph, Penn Valley, PA (US); Richard William Berenson, Waban, MA (US); Bruce Frank, Indianapolis, IN (US); Michael A. Weiss, Moreland Hills, OH (US); Thomas Hattier, Cleveland Heights, OH (US); Gregory Dubé, Littleton, MA (US); Zhiqiang Chen, Cleveland, OH (US)

(73) Assignee: THERMALIN DIABETES, INC., Waban, MA (US)

( * ) Notice: Subject to any disclaimer, the term of this patent is extended or adjusted under 35 U.S.C. 154(b) by 0 days.

(21) Appl. No.: 15/110,758

(22) PCT Filed: Jan. 13, 2015

(86) PCT No.: PCT/US2015/011202
§ 371 (c)(1),
(2) Date: Jul. 11, 2016

(87) PCT Pub. No.: WO2015/106269
PCT Pub. Date: Jul. 16, 2015

(65) Prior Publication Data
US 2016/0375104 A1   Dec. 29, 2016

Related U.S. Application Data

(60) Provisional application No. 61/926,944, filed on Jan. 13, 2014, provisional application No. 61/926,946, filed on Jan. 13, 2014.

(51) Int. Cl.
| | | |
|---|---|---|
| *A61K 38/00* | (2006.01) | |
| *A61K 38/28* | (2006.01) | |
| *A61K 9/00* | (2006.01) | |
| *A61K 36/05* | (2006.01) | |
| *A61K 36/23* | (2006.01) | |
| *A61K 47/18* | (2017.01) | |
| *A61K 45/06* | (2006.01) | |
| *A61K 47/12* | (2006.01) | |
| *A61K 47/20* | (2006.01) | |
| *A61K 47/36* | (2006.01) | |
| *A61M 5/142* | (2006.01) | |
| *A61M 5/172* | (2006.01) | |
| *A61M 25/02* | (2006.01) | |
| *A61M 37/00* | (2006.01) | |
| *A61N 1/04* | (2006.01) | |
| *A61N 1/32* | (2006.01) | |
| *A61N 7/00* | (2006.01) | |

(52) U.S. Cl.
CPC ............ *A61K 38/28* (2013.01); *A61K 9/0019* (2013.01); *A61K 9/0021* (2013.01); *A61K 36/05* (2013.01); *A61K 36/23* (2013.01); *A61K 45/06* (2013.01); *A61K 47/12* (2013.01); *A61K 47/183* (2013.01); *A61K 47/20* (2013.01); *A61K 47/36* (2013.01); *A61M 5/142* (2013.01); *A61M 5/1723* (2013.01); *A61M 25/02* (2013.01); *A61M 37/0092* (2013.01); *A61N 1/0448* (2013.01); *A61N 1/327* (2013.01); *A61N 7/00* (2013.01); *A61M 2025/0253* (2013.01); *A61M 2037/0007* (2013.01); *A61M 2205/055* (2013.01); *A61M 2205/35* (2013.01); *A61M 2205/50* (2013.01); *A61M 2205/502* (2013.01); *A61M 2230/201* (2013.01)

(58) Field of Classification Search
CPC .... A61K 2300/00; A61K 38/28; A61K 36/05; A61K 36/23; A61K 47/183; A61K 9/0019; A61K 45/06; A61K 47/12; A61K 47/20; A61K 47/36; A61K 9/0021; A61K 9/08; A61M 2025/0253; A61M 2037/0007
USPC .......................................................... 514/1.1
See application file for complete search history.

(56) References Cited

U.S. PATENT DOCUMENTS

| 5,461,031 A | 10/1995 | De Felippis |
|---|---|---|
| 8,192,957 B2 | 6/2012 | Weiss |
| 8,343,914 B2 | 1/2013 | Weiss |
| 8,399,407 B2 | 3/2013 | Weiss |

(Continued)

FOREIGN PATENT DOCUMENTS

| WO | 2015106269 A2 | 7/2015 |
|---|---|---|
| WO | 2016057529 A2 | 4/2016 |

(Continued)

OTHER PUBLICATIONS

American Diabetes Association. Continuous Subcutaneous Insulin Infusion. Diabetes Care, 2004. vol. 27, Supplement 1, p. S110.*
Pohl et al. Ultra-Rapid Absorption of Recombinant Human Insulin Induced by Zinc Chelation and Surface Charge Masking. Journal of Diabetes Science and Technology, Jul. 2012. vol. 6, Issue 4, pp. 755-763.*

(Continued)

*Primary Examiner* — Marcela M Cordero Garcia
(74) *Attorney, Agent, or Firm* — Morgan Lewis & Bockius LLP

(57) ABSTRACT

The present invention provides rapid-acting insulin and insulin analog formulations. The invention further provides delivery devices, particularly infusion sets, which allow for the rapid absorption of insulin and insulin analogs, as well as other active agents. Methods of using the insulin and insulin analog formulations as well as the insulin delivery devices for treating subjects with diabetes mellitus are also provided.

27 Claims, 26 Drawing Sheets

(56) References Cited

U.S. PATENT DOCUMENTS

| | | |
|---|---|---|
| 8,501,440 B2 | 8/2013 | Weiss |
| 8,921,313 B2 | 12/2014 | Weiss |
| 8,993,516 B2 | 3/2015 | Weiss |
| 9,079,975 B2 | 7/2015 | Weiss |
| 9,200,053 B2 | 7/2015 | Weiss |
| 9,138,479 B2 * | 9/2015 | Prestrelski ............ A61K 38/28 |
| 9,388,228 B2 | 7/2016 | Weiss |
| 9,487,572 B2 | 11/2016 | Weiss |
| 9,499,600 B2 | 11/2016 | Weiss |
| 2005/0176621 A1 * | 8/2005 | Brader ................. A61K 9/0019 514/5.9 |
| 2008/0090753 A1 | 4/2008 | Pohl et al. |
| 2010/0227795 A1 * | 9/2010 | Steiner ................. A61K 9/0019 514/6.4 |
| 2011/0195896 A1 | 8/2011 | Weiss et al. |
| 2012/0184488 A1 | 7/2012 | Weiss |
| 2013/0085101 A1 | 4/2013 | Weiss |
| 2014/0323398 A1 | 10/2014 | Weiss |
| 2015/0299286 A1 | 10/2015 | Weiss |
| 2015/0299287 A1 | 10/2015 | Weiss |
| 2015/0353621 A1 | 12/2015 | Weiss |
| 2015/0361153 A1 | 12/2015 | Weiss |
| 2016/0083448 A1 | 3/2016 | Weiss |

FOREIGN PATENT DOCUMENTS

| | | |
|---|---|---|
| WO | 2016064606 A1 | 4/2016 |
| WO | 2016105545 A2 | 6/2016 |
| WO | 2016118631 A1 | 7/2016 |

OTHER PUBLICATIONS

Krasner et al., "A Review of a Family of Ultra-Rapid-Acting Insulins: Formulation Development", Journal of Diabetes Science and Technology, 2012, vol. 6, No. 4, pp. 786-796.

International Search Report and Written Opinion for PCT Application No. PCT/US15/11202, dated Aug. 28, 2015, 10 pages.

* cited by examiner

A

| Insulin Analog | Well | Charge | Distance (cm) | % of Lispro |
|---|---|---|---|---|
| Lispro | 3 | -2 | 1.5 | 100 |
| Fluorolog | | -3.3 | 1.8 | 120 |
| Hexalog-1 | 1 | -4 | 2.2 | 146 |
| Hexalog-2 | 2 | -5 | 2.6 | 173 |

B

RAPID ACTION INSULIN FORMULATIONS AND PHARMACEUTICAL DELIVERY SYSTEMS

RELATED APPLICATIONS

This application claims the benefit of U.S. Provisional Patent Application No. 61/926,944, filed Jan. 13, 2014, and U.S. Provisional Patent Application No. 61/926,946, filed Jan. 13, 2014, each of which are hereby incorporated by reference in their entireties.

STATEMENT REGARDING FEDERALLY SPONSORED RESEARCH OR DEVELOPMENT

This invention was made partially with government support under SBIR grants awarded by the National Institutes of Health under grant numbers 1R43DK092041, 1R43DK088506, 1R43DK094668, 5R44DK088506, 5R43DK094668, 1R43DK100186, 1R43DK100190, 2R44DK092041, 1R43DK103445, 1R41DK081292, and 1R43DK089831. The U.S. government has certain rights to the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (TRD-001-SequenceListing.txt, date recorded: Jan. 6, 2017, file size 8.00 kilobytes).

TECHNICAL FIELD

The present invention relates in part to pharmaceutical formulations and delivery systems.

BACKGROUND

Diabetes mellitus denotes a spectrum of metabolic diseases characterized by abnormally high blood glucose levels. There are two major types of diabetes. Type 1 diabetes results from the body's failure to produce insulin. For these patients, administration of insulin is the only available therapy. Type 2 diabetes typically begins with insulin resistance, a condition in which the body's cells fail to respond to insulin. As the disease progresses, a relative or absolute lack of insulin production also develops. Type 2 diabetes is often associated with excessive body weight and lack of exercise. The treatment for Type 2 diabetes typically starts with exercise and diet management as well as medications without insulin. As the disease deteriorates, many patients with Type 2 diabetes eventually require insulin therapy to support their metabolism.

In healthy individuals, insulin secretion is closely tied to blood glucose level. Increased glucose level, for example, after meals, is compensated by a rapid increase in insulin release within minutes of glucose entry into the blood. In the fasting state, insulin level falls to a basal level, which is sufficient to guarantee a continuous supply of glucose to insulin-sensitive organs and tissues. The objective of insulin therapy is to replicate this natural time-action profile of insulin in diabetic patients, such that blood glucose level can stay within the normal range characteristic of healthy individuals. However, current insulin products and delivery systems do not sufficiently meet this objective due to limitations in the absorption of the insulin or insulin analogue.

For example, when insulin is solubilized in a buffer without zinc and stored at room temperature (25-30° C.), the insulin will begin to form amyloid fibrils within 7-14 days. To avoid this problem, currently available insulin products are typically formulated with zinc, which forms a complex with insulin called a zinc-insulin hexamer. Zinc-insulin hexamers can be stable in solution at room temperature for greater than 30 days, which is long enough to meet regulatory requirements for insulin formulation stability. However, zinc-insulin hexamers are too large to be readily absorbed by capillaries, and so the hexamers must disassemble after injection before the insulin can be absorbed. This prevents these formulations from being absorbed quickly enough.

Accordingly, there is an unmet need for insulin compositions, formulations, and delivery systems that better replicate the natural time-action profile of insulin.

SUMMARY OF THE INVENTION

The present invention relates in part to rapid-acting insulin compositions, formulations and delivery systems that better replicate the natural activity profile of insulin (i.e., on pancreatic secretion in human subjects without diabetes mellitus). The invention especially relates to prandial insulin administered before or during meals to diabetic patients. In various aspects, the invention provides insulin compositions, formulations, delivery systems, and methods of treatment that provide for the rapid absorption of insulin and insulin analogues. When used in combination with a basal insulin formulation in some embodiments, or in an artificial pancreas system, the invention provides for tighter control of glucose levels.

In other aspects, the invention provides infusion sets that enhance the absorption of pharmaceutical formulations (including but not limited to insulin) through energy delivery systems.

In various aspects and embodiments, the invention provides for an onset of insulin activity of less than about 40 minutes after administration, and in some embodiments the onset of activity is within about 30 minutes, or within about 20 minutes, or within about 15 minutes after administration. In some embodiments, the insulin reaches $T_{max}$ at less than about 60 minutes after administration, and less than about 40 minutes in some embodiments. In further embodiments, the invention provides a duration of insulin activity of about five hours or less, including about three hours or less or about two hours or less in some embodiments.

In one aspect, the invention provides a pharmaceutical composition comprising an effective amount of a monomeric insulin analogue and one or more calcium ion-chelating agents and/or charge-masking agents. In various embodiments, the pharmaceutical composition or formulation is a substantially zinc-free formulation, thereby avoiding insulin hexamer assembly. The pharmaceutical compositions of the present invention comprise a monomeric insulin analogue which may have one or more mutations that reduce or eliminate fibril formation or reduce the formation of degradation products such as covalent dimers/polymers or related substances, thus maintaining stability of the insulin in a monomeric or dimeric state. In some embodiments, the insulin is a single-chain insulin analogue or an insulin analogue with natural or non-natural amino acid mutations. Various insulin analogues that find use with the various aspects of the invention are described in detail herein. In various embodiments, the monomeric insulin analogue is formulated at from about U10 to about U2000. In various embodiments, the insulin analogue is formulated at U100 or greater (e.g., about U200, about U300, about U400, about U500, about U1000, about U1500, or about U2000) without significant fibril formation. For example, in various embodiments, the pharmaceutical composition is stable for at least about 1 month, at least about 6 months, at least about 9 months, or at least about 12 months at 25° C. without substantial formation of insulin fibrils.

The pharmaceutical composition of the invention includes one or more calcium ion-chelating agents and/or charge-masking agents. In some embodiments, the agent includes one or more amino organic acids, ionic salts (e.g., comprising cations of Na, K, Mg, etc.), polycarboxylic acid compounds, anionic polysaccharides, organosulfur compounds, di- or tri-carboxylic acids, penicillamine, and extract or partial extract of chlorella and/or cilantro. In various embodiments, without being limited by theory, the agent masks charges in the subcutaneous tissue, which allows charged surfaces on insulin and insulin analogues to avoid being "trapped" by charged elements in the tissue or interstitial fluid and to more rapidly move toward the blood or lymphatic vessels for absorption. In some embodiments, without being limited by theory, the chelation of calcium ions in the subcutaneous tissue promotes disassembly of adherens junctions and tight junctions (i.e., protein complexes at cell-cell junctions linked to the cellular cytoskeleton), and other forms of tight junctions between cells, for example in the vessel endothelium, thereby increasing the rate of insulin absorption. The compositions and formulations of the invention can be packaged in solution form, including sterile vials and pre-filled injection pens or cartridges, and may be used with infusion sets employing an insulin pump.

In another aspect, the present invention provides an infusion set which may be used with a rapid-acting insulin formulation as well as other pharmaceutical formulations, and one or more energy-delivery systems such as an ultrasound transducer, a tactor, and an electrophoresis electrode. The energy-delivery system increases absorption of the pharmaceutical formulation by promoting the migration of the active agent to the vasculature from a subcutaneous depot or by increasing blood circulation to the area. The ultrasound transducer may be a low intensity ultrasound (LITUS) transducer, and the tactor may be a low-frequency piezoelectric tactor.

In various embodiments, the infusion set comprises a first body, an adhesive surface, a subcutaneous infusion catheter, and one or more of an ultrasound transducer, a tactor, and an electrophoresis electrode. In certain embodiments employing electrophoresis, the infusion set includes a first electrophoresis electrode proximal to the distal end of the infusion catheter (e.g., a cathode), and a second electrophoresis electrode on or near the skin surface (e.g., an anode), which can be attached to the adhesive surface of the infusion set. This design will promote, for example, insulin migration (especially negatively charged insulin analogs) from the tip of the catheter toward the vessels at the top of the subcutis. In some embodiments, the insulin analogue (or other active agent) has a net charge in the range of −2 to −6. In some embodiments, the insulin formulation exhibits increased hexamer disassembly, or is a monomeric insulin analogue that is stable and provided in a substantially zinc-free formulation that avoids hexamer assembly.

Other aspects of the invention will be apparent from the following detailed description of the invention.

DESCRIPTION OF THE FIGURES

FIGS. 8A and 8B show the top and side views, respectively, of a configuration with the anode (5) placed on the adhesive patch away from the infusion set head. FIG. 8C show a configuration with the anode placed directly over the infusion site.

FIG. 11A is a table of results, including a key to the wells shown in FIG. 11B. FIG. 11B is a picture of an exemplary acrylamide gel.

Figure 16:
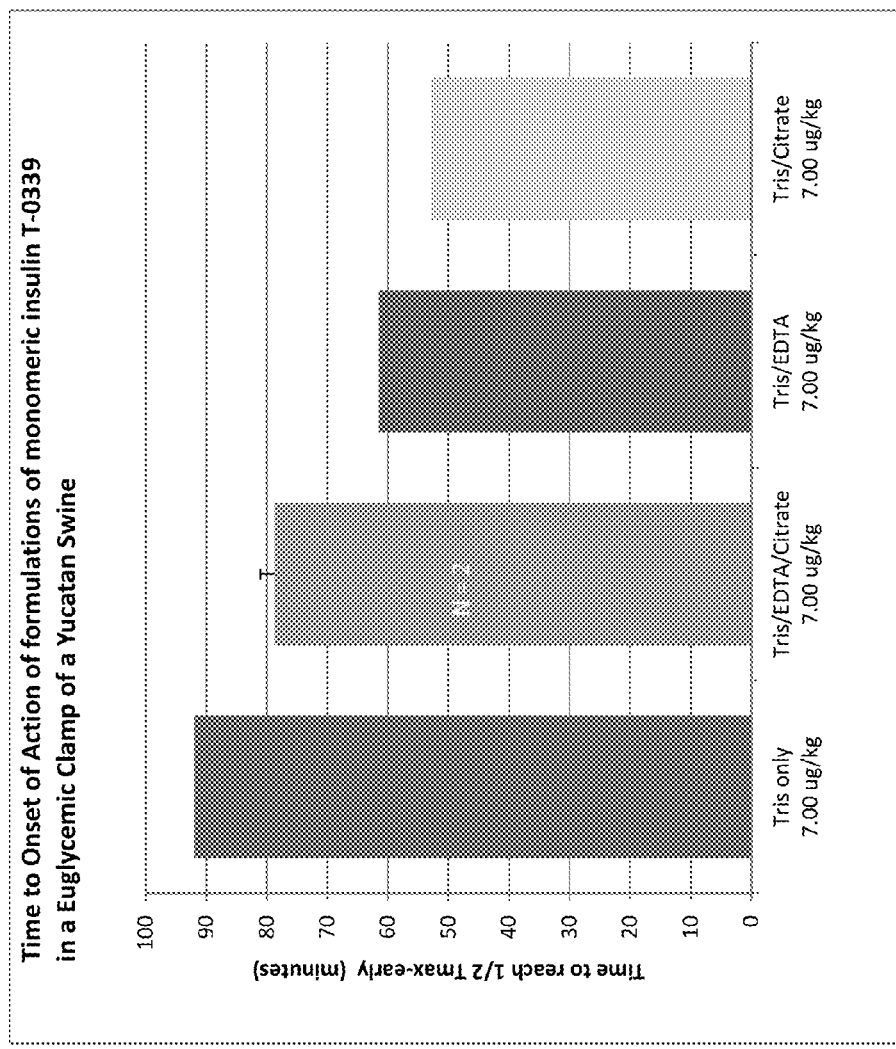

FIG. 16 shows the effect of various charge-blocking excipients on the onset of action after subcutaneous injection of monomeric insulin analog T-0339.

Figure 17A:
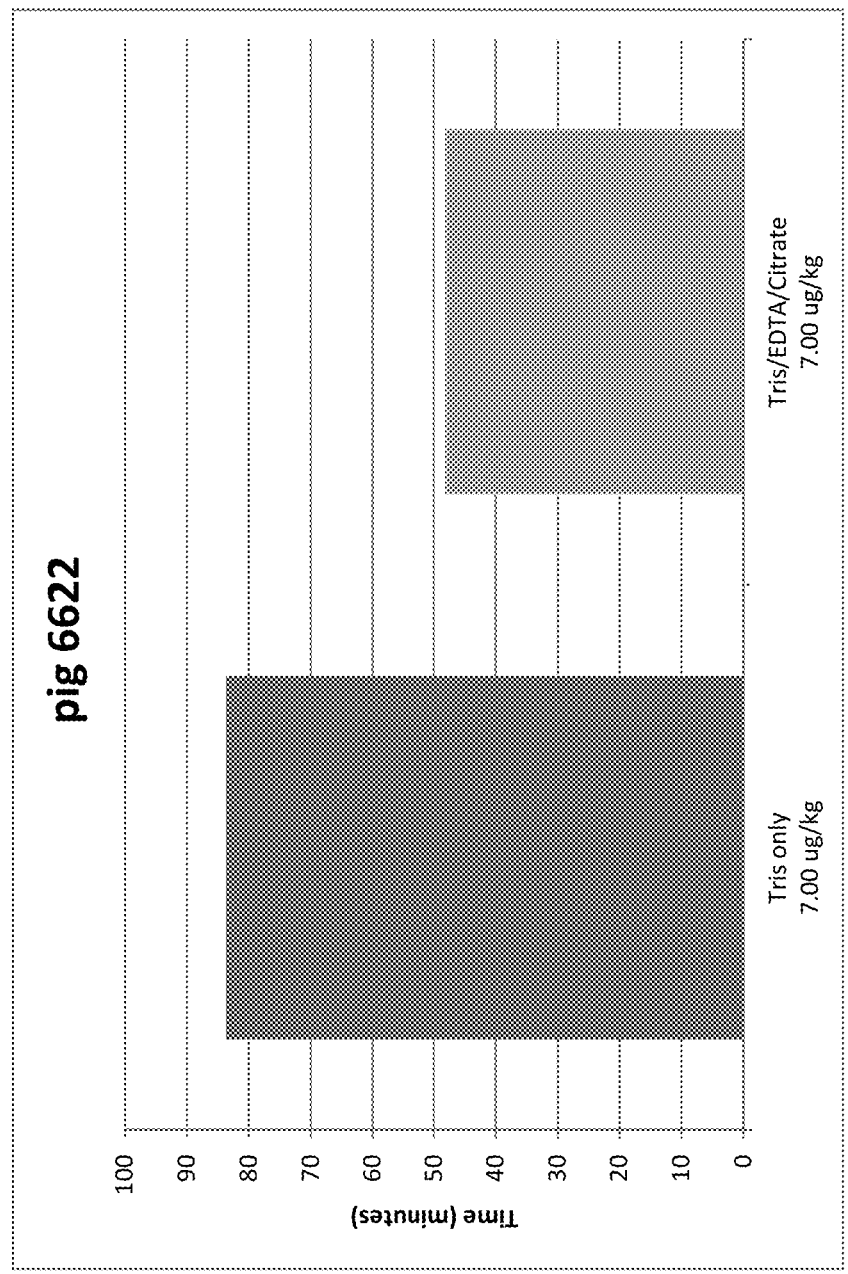
Figure 17B:
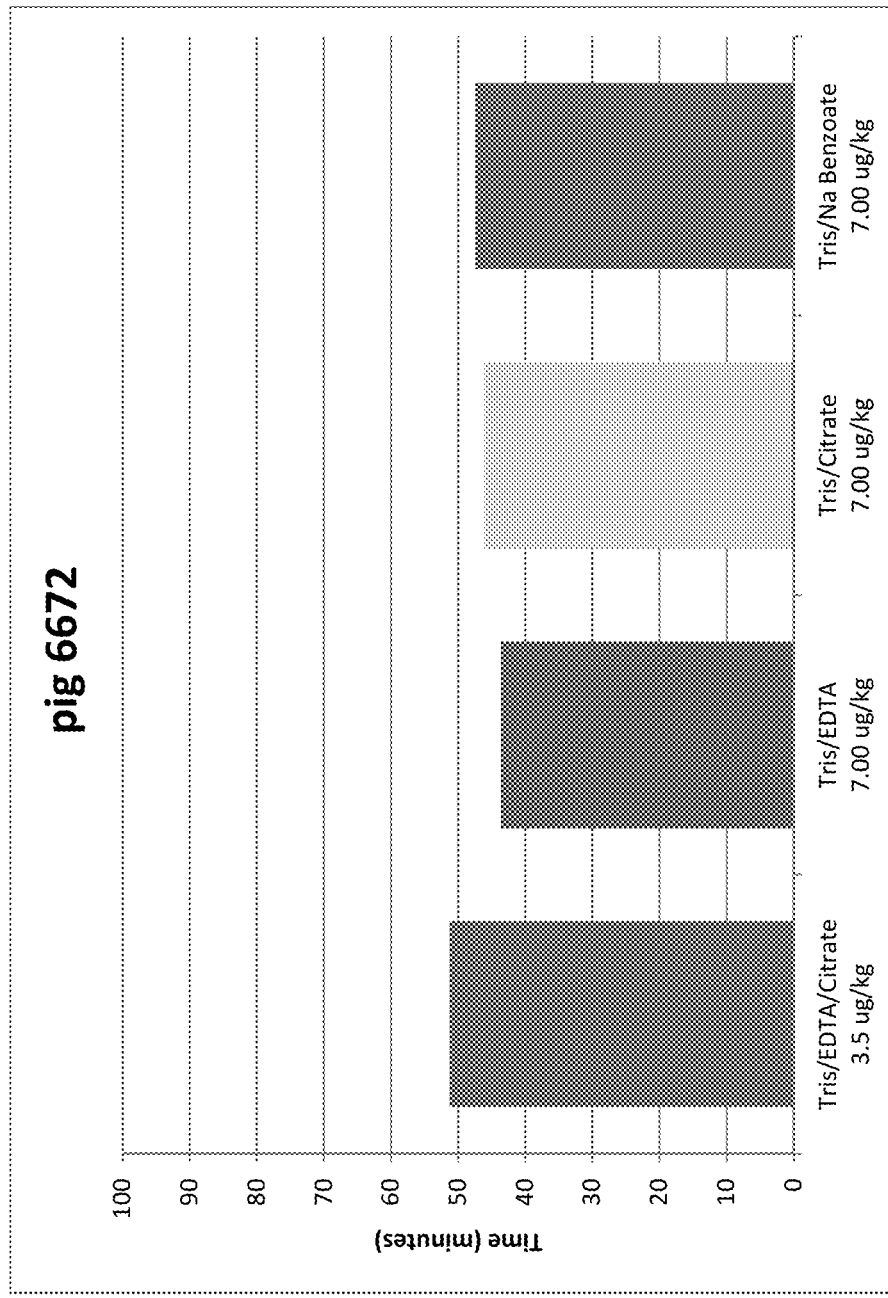
Figure 17C:
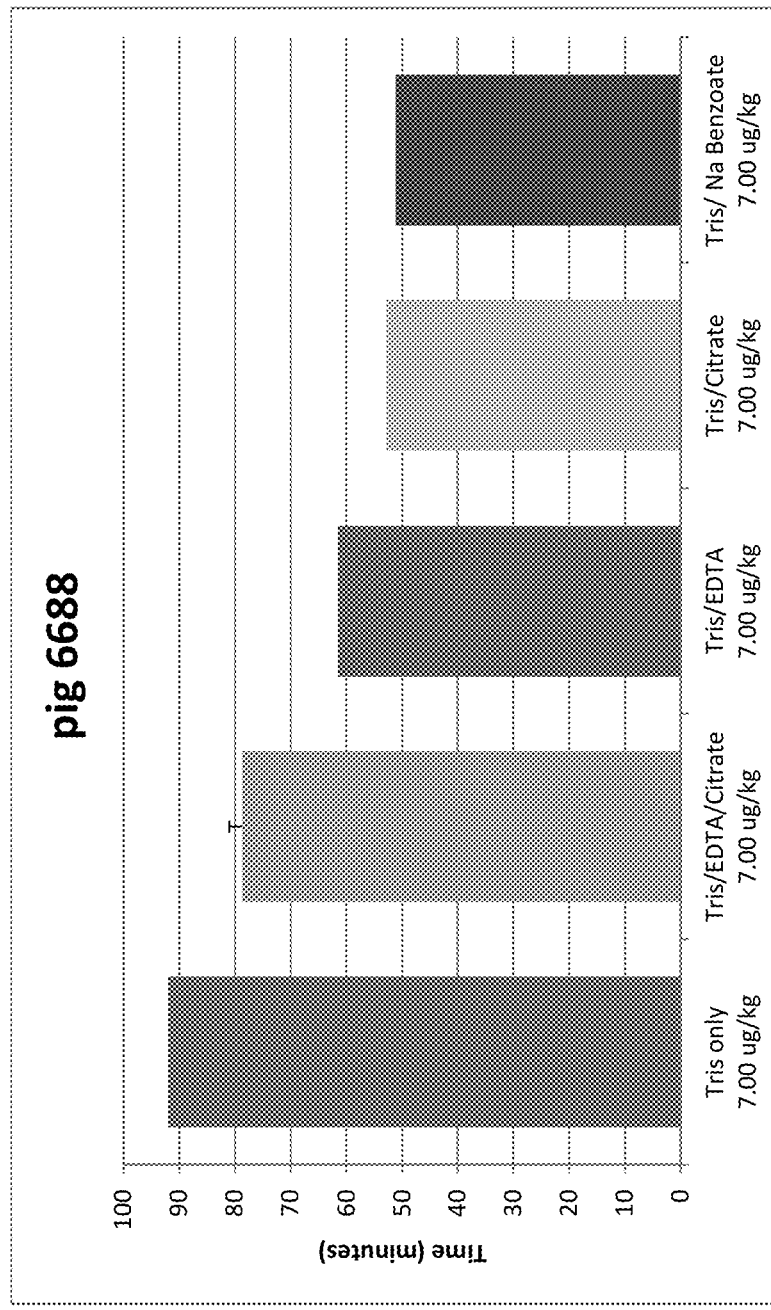

FIGS. 17A-C shows the effect of various charge-blocking excipients on the onset of action ($T_{max}$ ½ early) after subcutaneous injection of monomeric insulin analog T-0339 (U500), in three pig studies. +SEM error bars displayed if n>1.

Figure 18A:
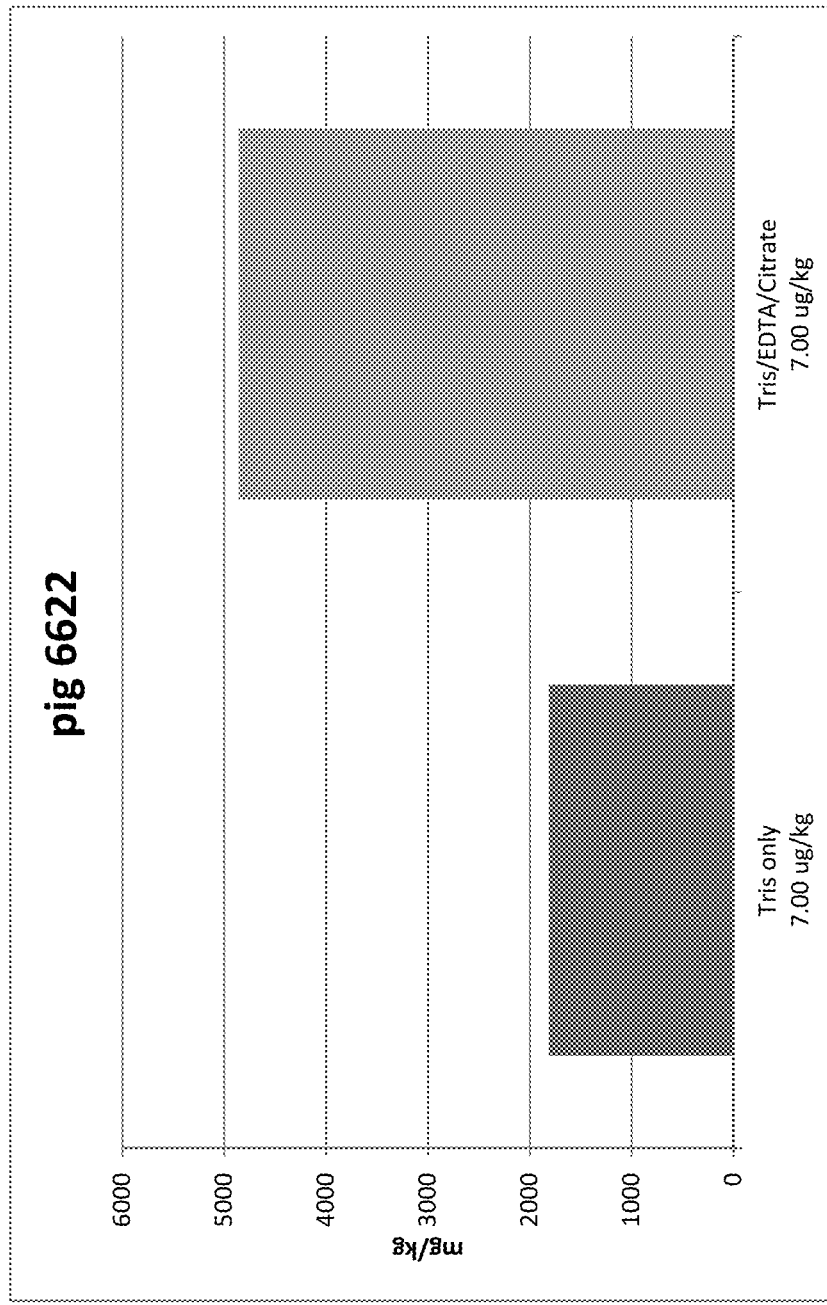
Figure 18B:
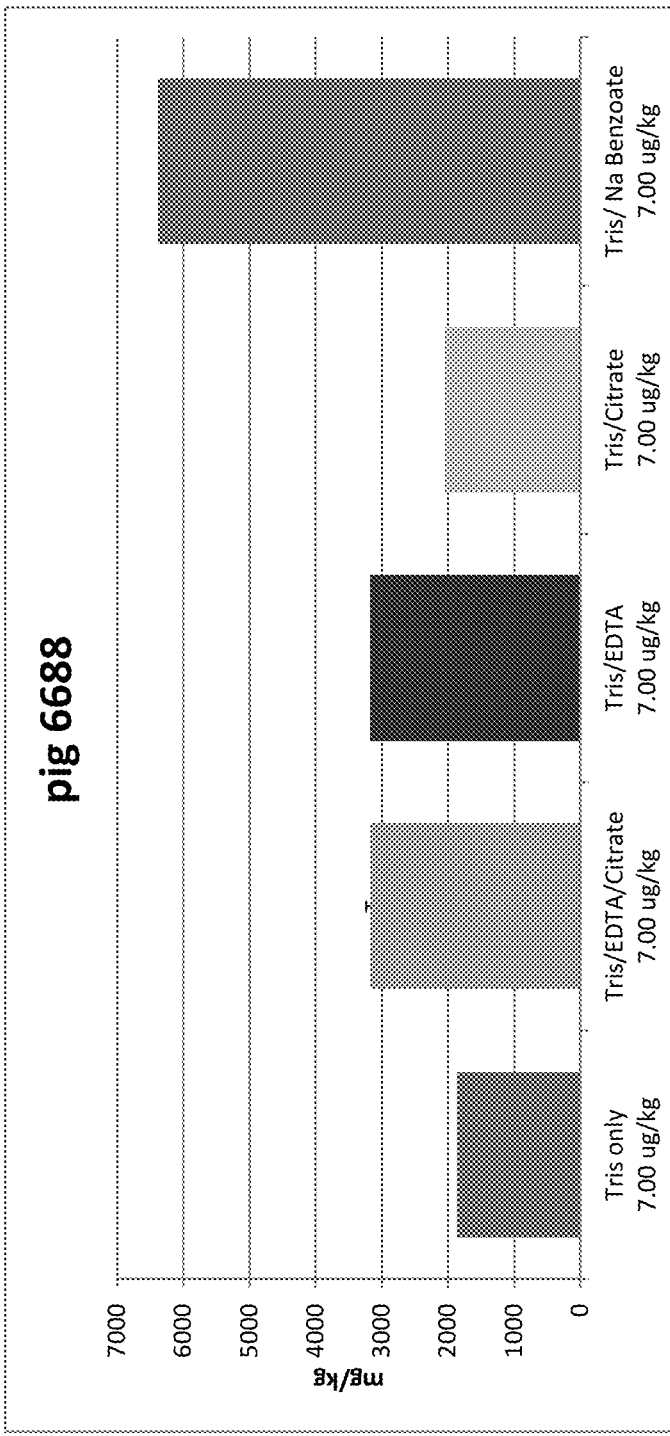
Figure 18C:
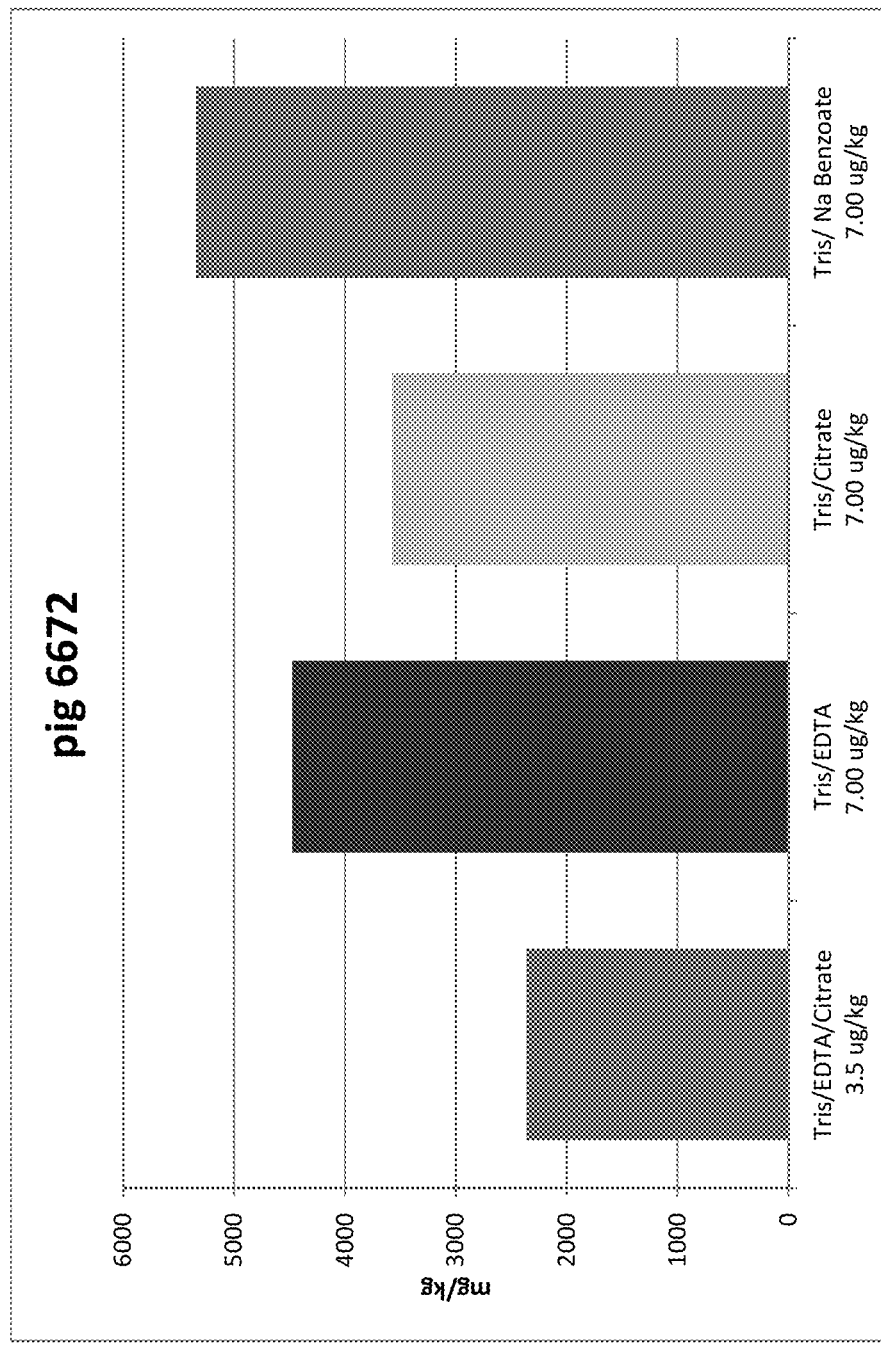

FIG. 18A-C shows AUC ½ late for the same pig studies of FIG. 17. +SEM error bars displayed if n>1.

Figure 19A:
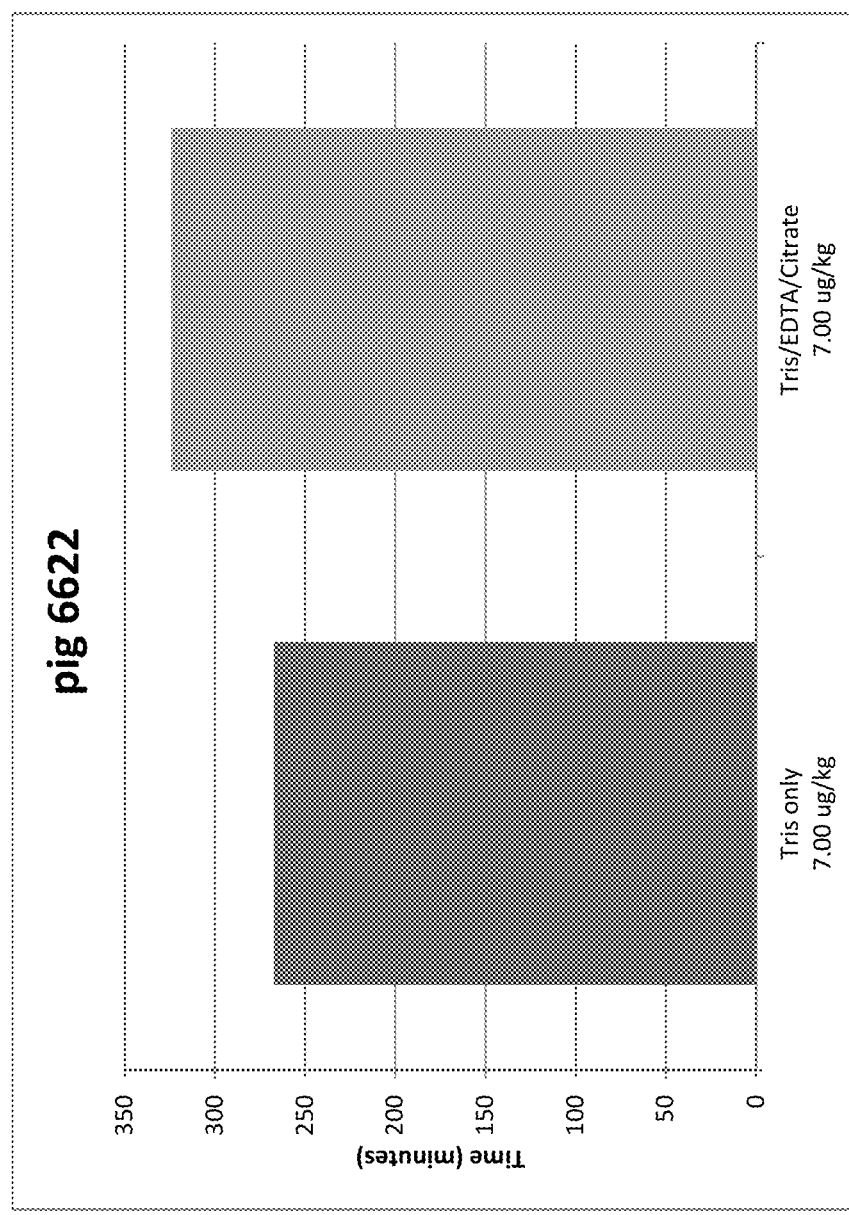
Figure 19B:
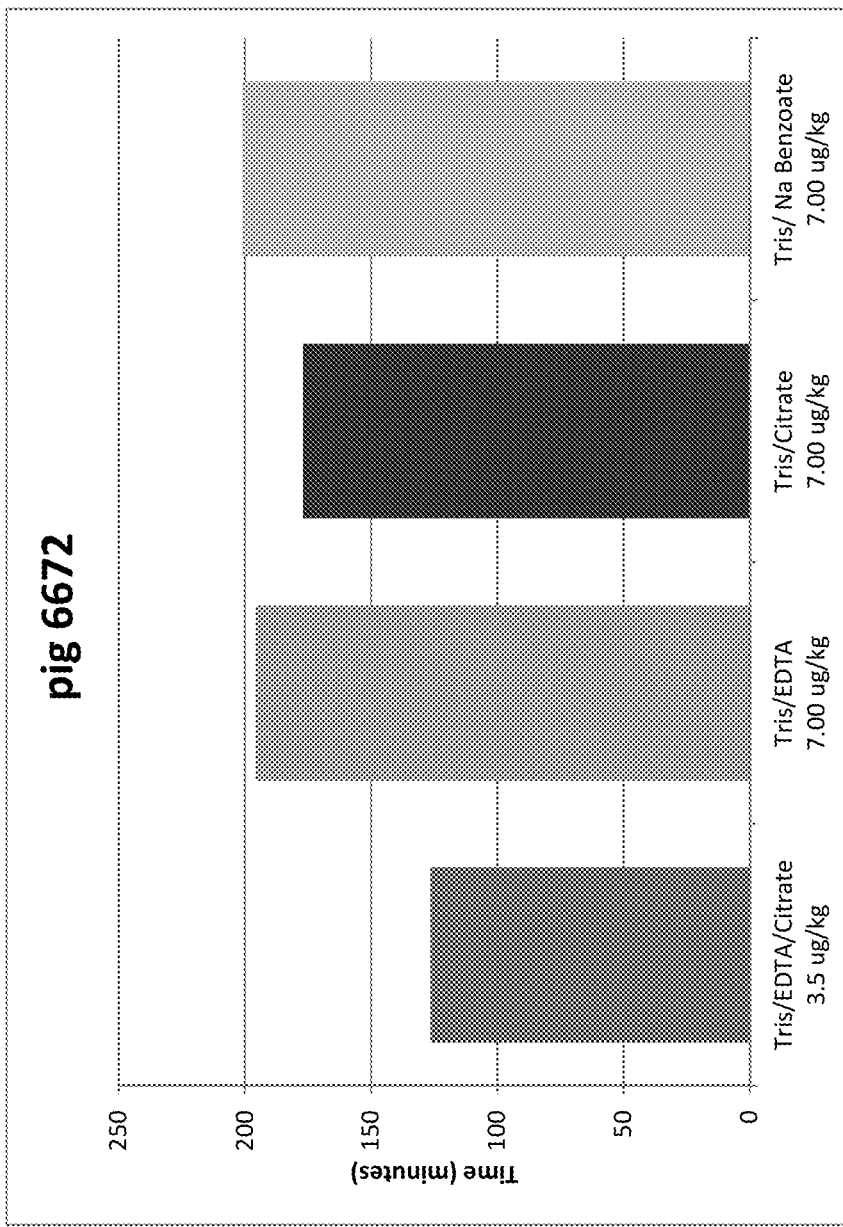
Figure 19C:
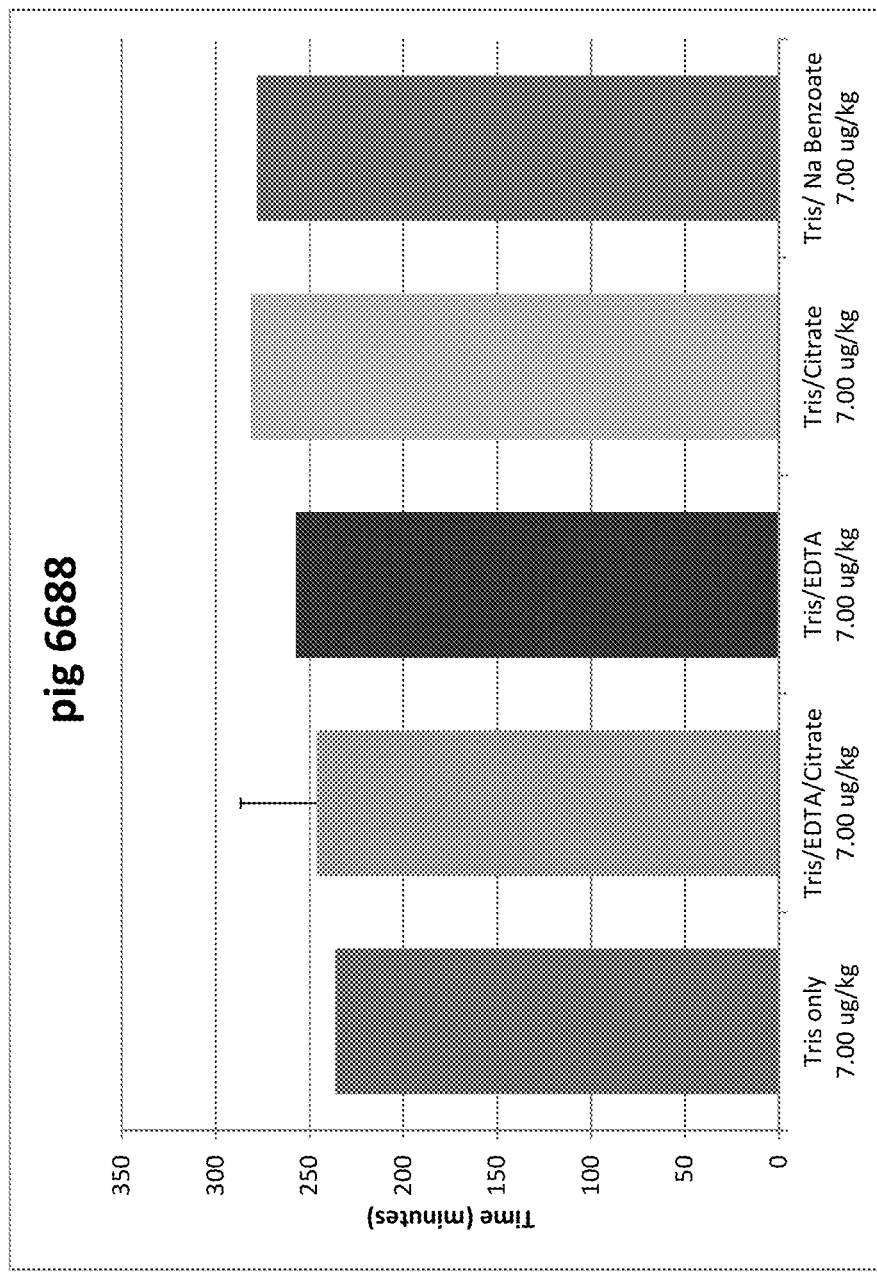

FIG. 19A-C shows the $T_{max}$ ½ late for the same pig studies of FIG. 17. +SEM error bars displayed if n>1.

DETAILED DESCRIPTION

The present invention provides rapid-acting insulin, and insulin analogue formulations. The invention further provides delivery devices, particularly infusion sets, that promote the rapid absorption of insulin and insulin analogues (or other pharmaceutical formulation), including monomeric insulin analogues. Methods of using the insulin and insulin analogue formulations as well as the insulin delivery devices for treating subjects with diabetes are also provided.

Insulin therapy has been used for more than 90 years to treat diabetes. Typically, therapy involves multiple insulin injections every day. According to the conventional regimen, patients are treated with one or two daily insulin injections of long-acting insulin to cover the basal insulin requirement supplemented with injections of a fast-acting insulin formulation (or fast-acting insulin analogue formulation) to cover the insulin requirement related to meals. However, even when properly and timely administered, insulin injections often do not mimic the natural action profile of insulin. For example, available rapid-acting insulin analogues enter into blood and the site of action too slowly, and have too long an overall duration of action. This results in inadequate insulin levels at the initiation of a meal and too much insulin present between (and particularly immediately after) meals. In turn, this lag in insulin delivery causes hyperglycemia early after starting a meal and hypoglycemia after meals.

Figure 1:
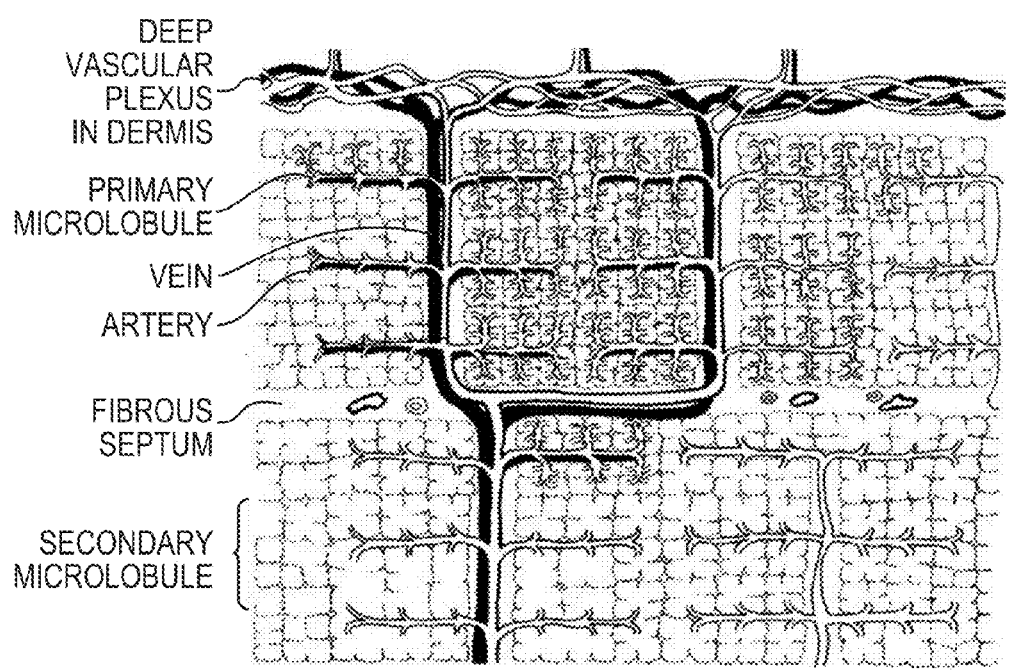
FIG. 1 is a diagram of the anatomy of the skin.

Insulin is typically delivered through the subcutaneous tissue. The subcutaneous tissue ("subcutis" or "s.q.") sits below the epidermis (which is about 0.05 to 1 mm thick) and the dermis (which is about 0.3-3 mm thick) and consists of fat lobules separated by fibrous septae. Individual lobules may be up to 3 mm thick and are made up of primary and secondary microlobules (FIG. 1). The entire subcutis may be between 3 and 20 mm thick. Blood supply is relatively sparse (especially compared to the dermis), although there are typically vessel plexi at the top (near the interface with the dermis) and bottom of the subcutis. There are lymphatic vessels in the subcutis as well.

Figure 2:
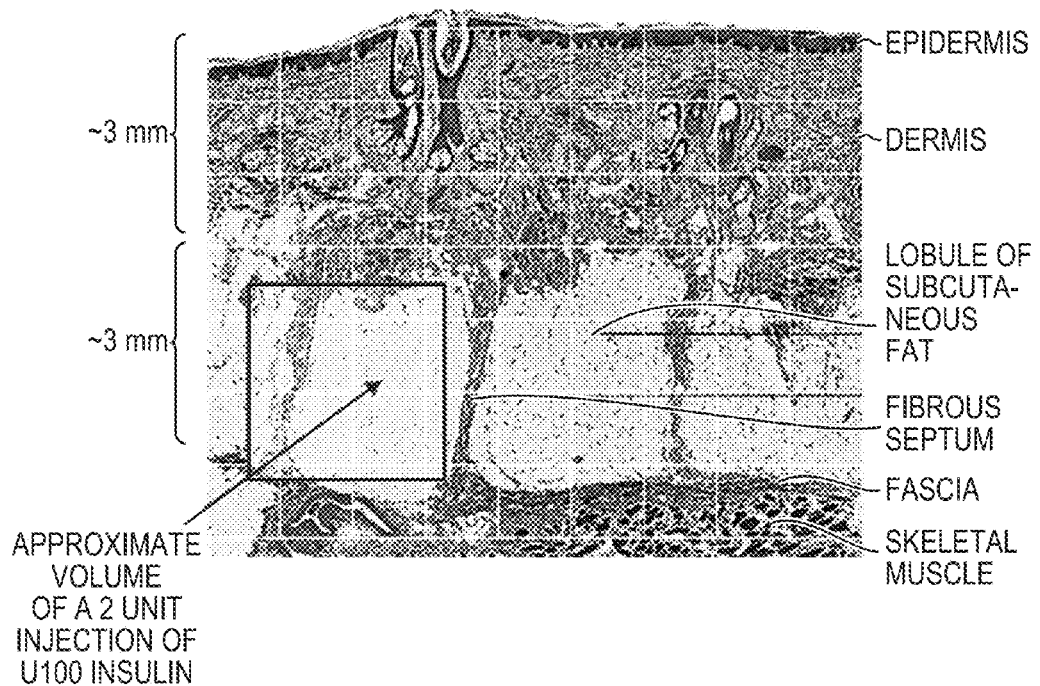
FIG. 2 shows a histological section of skin, and the approximate volume of an insulin injectate.

Subcutaneous delivery can be achieved by needles (typically 3-13 mm long) for individual injections or by infusion catheter (which are typically 6-9 mm long), e.g., for continuous subcutaneous insulin infusion (CSII). The latter is connected to an infusion set connected to an insulin pump and is typically placed using an insertion device. In both cases, insulin is delivered into the tissue from the distal end of the lumen, which is between 2 and 11 mm from the skin surface. The lumen is typically between 0.2 and 0.4 mm in diameter. For CSII, basal insulin is delivered as frequent micro-boluses of rapid-acting insulin. However, all mealtime insulin analogue formulations are typically delivered as a bolus, typically with an injection volume of between 20 and 500 which fills an area about 2.7 to 8 mm in diameter (FIG. 2).

An infusion set typically comprises a first body with an adhesive surface to adhere to the epidermis, an infusion catheter that is inserted through the epidermis and dermis into the subcutis (often using an insertion device), and a supply tube in continuous fluid contact with the catheter. Infusion sets are typically placed once a day or once every other day. An infusion set can be used to deliver any liquid pharmaceutical formulation into the subcutis.

Insulin boluses initially pool (form a depot) near the end of the lumen, thereby displacing and compressing the local fat lobules and stretching the local septae. The insulin then must diffuse through the base substance in the septae in order to reach capillaries and venules, where it is eventually absorbed through the vessel lumens into the blood. Absorption into blood vessels is difficult since the vessels have positive fluid pressure and are more likely to leak than absorb. Insulin hexamers are too big to be absorbed, and so hexameric insulin formulations must disassemble into dimers or monomers before the insulin can be absorbed.

The rapidity of insulin action largely depends on how quickly it is absorbed from the subcutis. The active form of insulin in the blood stream is the monomer. However, insulin formulations (or insulin analogue formulations) containing a predominance of protein molecules in the forms of monomers and dimers ordinarily have a strong tendency to aggregate and form inactive fibrils. Thus, typical commercial insulin formulations at 100 IU/mL (i.e., U100) are composed of hexamers with two zinc atoms that stabilize the molecular assembly and its component monomeric units. Insulin formulations prepared in the form of zinc hexamers have a sufficient shelf life (e.g., 30 days at 30° C.), but are not readily absorbed largely due to their size. The hexamers must first disassemble for absorption through blood vessels.

Attempts have been made to ameliorate this problem. For example, WO 2007/121256 and WO 2010/102020 teach mixing a hexameric insulin with EDTA and citrate before administration, with the objective of chelating the zinc out of the hexamers and masking charges on the insulin to inhibit hexamer formation, thereby forcing pre-injection hexamer disassembly. Although this approach may speed insulin absorption, it also destabilizes the insulin formulation or requires mixing excipient with the hexameric insulin before each administration. Not only are such strategies undesirable in terms of patient convenience and compliance, but such strategies are also poor candidates for insulin pump systems and for use in continuous or automated delivery systems.

However, even in the case of monomeric and/or dimeric insulin analogue formulations, wherein hexamer disassembly is not relevant, insulin action after subcutaneous injection is not as fast as insulin action when delivered directly to the bloodstream (e.g., by i.v. infusion). Thus, hexamer disassembly is not the only factor limiting the rate of insulin absorption upon subcutaneous administration.

Most models of insulin absorption assume that virtually all subcutaneous insulin molecules are absorbed into the capillaries. However, studies in sheep suggest that as much as half of insulin is, in fact, absorbed through the lymphatic vessels (See, Charman S, et al., (2001) *Pharmaceutical Research*, 18(11): 1620-1626). The lymphatic system is designed to facilitate reabsorption of excess fluid and large proteins in the interstitial space. Insulin hexamers, as well as insulin dimers (which may be less readily absorbed by capillaries than monomers) may be disproportionately shunted into lymphatic absorption. The path to and through the lymphatic system may be longer and involve a greater lag time between injection and general blood circulation than does the path directly to blood vessels via subcutaneous capillaries.

Figure 3:
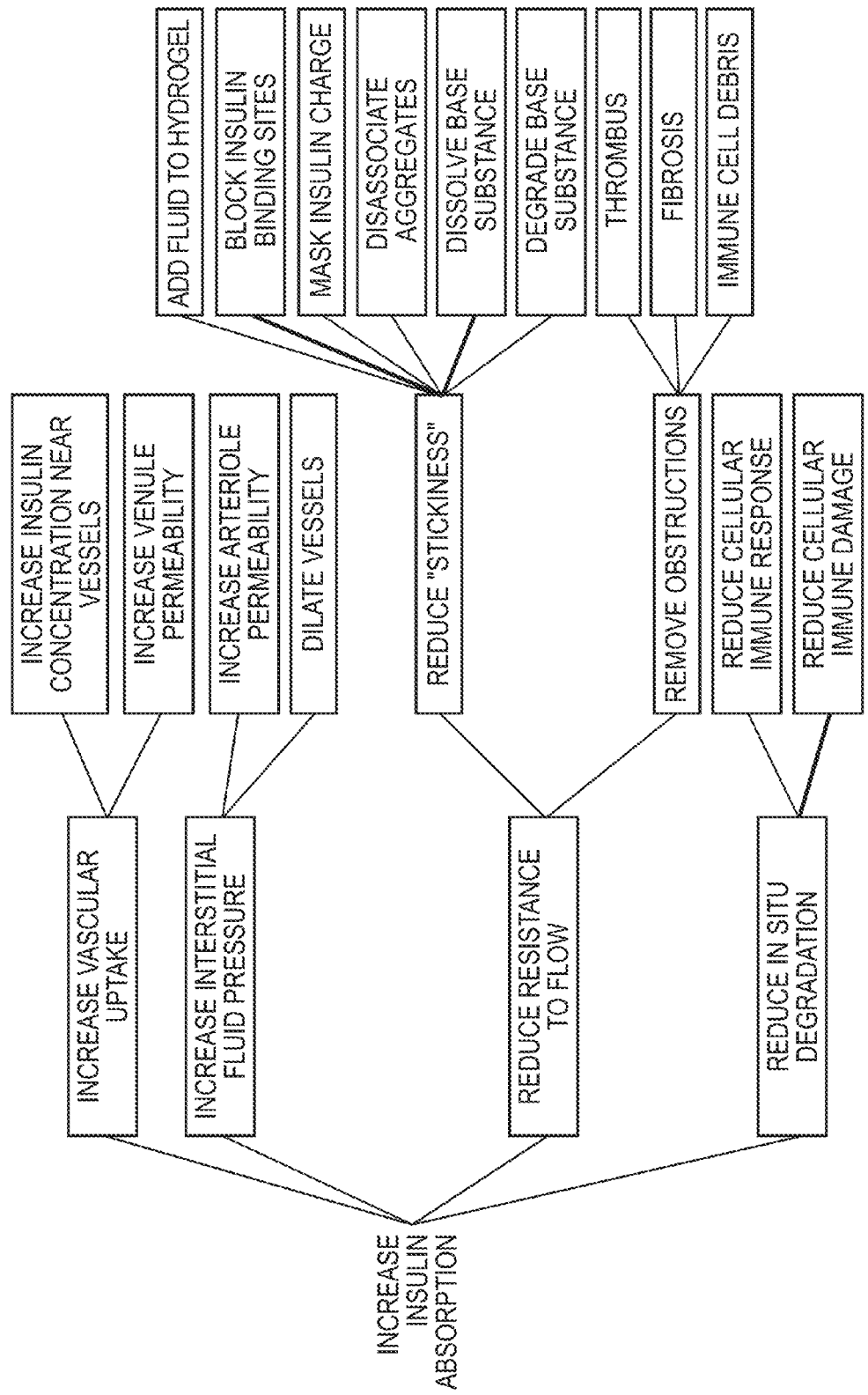
FIG. 3 shows a cause and effect tree identifying potential strategies for increasing the absorption of subcutaneously administered insulin.

Various factors that may influence the rate at which insulin molecules are absorbed into the blood from a subcutaneous depot are depicted in FIG. 3. For example, insulin absorption can be enhanced by increasing vascular uptake, either by increasing insulin concentration near blood vessels or by increasing vascular permeability. Alternatively, insulin absorption can be enhanced by affecting interstitial fluid pressure, either by increasing arteriole permeability or by dilating vessels. Alternatively still, insulin absorption can be enhanced by reducing the resistance to flow, such as by reducing "stickiness" of insulin in the tissue, which can be accomplished, for example, by altering the viscosity of the depot, blocking insulin binding sites, masking insulin charge, masking the charge of the tissue, disassociating aggregates, and/or dissolve or degrade the base substance of the surrounding tissue or matrix. Alternatively, reduced resistance to flow might be accomplished by removing obstructions such as thrombus, fibrosis, or cellular debris (e.g., immune cell debris). In still other embodiments, the rate of insulin absorption is enhanced by reducing the cellular immune response and/or reducing cellular immune damage. Dampening of such biological processes in the subcutaneous space may also reduce in situ degradation and so increase the bio-availability of the injected insulin formulation.

In one aspect, the present invention provides a pharmaceutical composition comprising an effective amount of a monomeric insulin analogue and one or more calcium ion-chelating agents or charge-masking agents. Without being bound by theory, masking charges in the sub-cutaneous tissue enhances migration of the monomeric insulin through the subcutis toward the blood vessels, particularly if the monomeric insulin has charged regions that are surface exposed. Further, and without being limited by theory, by promoting a transient local disassembly of adherens junctions or tight junctions, for example in the vessel endothelium, by chelating cations (e.g., $Ca^{2+}$), the absorption of insulin can be improved.

Native human insulin contains two chains, an A chain, containing 21 residues and a B chain containing 30 residues. Insulin is normally stored in the pancreatic β-cell as a $Zn^{2+}$-stabilized hexamer, but functions as a $Zn^{2+}$-free monomer in the bloodstream. However, the monomer is most susceptible to fibrillation and chemical degradation, and thus insulin is generally formulated in its hexamer state with zinc, but often with mutations and/or formulation components that promote hexamer disassembly. However, even these insulin analogues (e.g., insulin lispro) exhibit some delay for hexamer disassembly, and thus exhibit a considerable delay in onset of action and "tail" in duration.

In various embodiments, the pharmaceutical composition comprises a monomeric insulin analogue. As used herein, a "monomeric insulin analogue" refers to an insulin that is stable for at least 30 days at 25° C. when it is formulated substantially without zinc (e.g., less than about 0.05 moles of zinc per mole of insulin) and thus present in solution predominately in the monomeric or dimeric form as opposed to the zinc-hexameric form. For example, the monomeric insulin analogue can be formulated at a high concentration, such as at 100 IU/mL (e.g., about U100) or greater (e.g., about U200, about U300, about U400, about U500, about U1000, about U1500, or about U2000) without significant fibril formation or chemical degradation. In various embodiments, the monomeric insulin is stable in the pharmaceutical composition for at least about 1 month, or at least about 2 months, or at least about 3 months, or at least about 4 months, or at least about 5 months, or at least about 6 months, or at least about 9 months, or at least about 12 months at 25° C. without substantial formation of insulin fibrils.

As used herein, the term "about" means + or −10% of the associated numerical value.

Accordingly, in various embodiments, the present invention contemplates the use of monomeric insulin analogues that have one or more mutations that reduce or eliminate fibril formation and/or attenuate chemical degradation, such as into other covalent dimer/polymer or related substances. The mutation(s) may be (independently) a natural or non-natural (e.g., non-genetically encoded) amino acid substitutions, insertions, or deletions. It is contemplated that the mutations can be introduced into the structure or sequence of any of the existing insulin or insulin analogues, particularly the known rapid-acting insulin products. For example, the mutations can be introduced into insulin analogues such as Lispro (KP) insulin (sold under the name Humalog®), Aspart insulin (sold under the name Novalog®), Glulisine insulin (sold under the name Apidra®), or other rapid-acting or prandial insulins, including native insulin (e.g., native human insulin).

In certain embodiments, the mutations include amino acid substitutions such as conservative amino acid substitutions, and/or non-conservative substitutions. "Conservative substitutions" include those substitutions made within a group of amino acids with similar side chains, for example: the neutral and hydrophobic amino acids glycine (Gly or G), alanine (Ala or A), valine (Val or V), leucine (Leu or L), isoleucine (Ile or I), proline (Pro or P), tryptophan (Trp or W), phenylalanine (Phe or F) and methionine (Met or M); the neutral polar amino acids serine (Ser or S), threonine (Thr or T), tyrosine (Tyr or Y), cysteine (Cys or C), glutamine (Glu or Q), and asparagine (Asn or N); basic amino acids lysine (Lys or K), arginine (Arg or R) and histidine (His or H); and acidic amino acids aspartic acid (Asp or D) and glutamic acid (Glu or E). Further, standard amino acids may also be substituted by non-standard amino acids, for example, those belonging to the same chemical class. By way of non-limiting example, the basic side chain lysine may be replaced by basic amino acids of shorter side-chain length (Ornithine, Diaminobutyric acid, or Diaminopropionic acid). Lysine may also be replaced by the neutral aliphatic isostere Norleucine (Nle), which may in turn be substituted by analogues containing shorter aliphatic side chains (Aminobutyric acid or Aminopropionic acid). In some embodiments, the insulin analogue has from one to five mutations with respect to the sequence of Insulin Lispro, Insulin Aspart, or Fluorolog (Asp B10, ortho-monofluorophenylalanine-B24, lispro insulin). In some embodiments, these mutations are conservative mutations, with no more than one, two, or three non-conservative mutations or non-standard mutations.

In various embodiments, the monomeric insulin analogue includes a B-chain polypeptide with mutations at positions corresponding to B24, B25, or B26 of native human insulin. For example, the monomeric insulin analogue may include a B-chain polypeptide that incorporates a halogenated phenylalanine substitution at position B24, B25, or B26. In one embodiment, the halogenated phenylalanine is located at position B24. The halogen may be fluorine, chlorine or bromine, for example. In an embodiment, the halogenated phenylalanine at B24 is a chlorinated phenylalanine or a fluorinated phenylalanine. In another embodiment, the halogenated phenylalanine is ortho-monofluoro-phenylalanine (2-fluoro-phenylalanine), ortho-monobromo-phenylalanine (2-bromo-phenylalanine), ortho-monochloro-phenylalanine (2-chloro-phenylalanine), para-monofluoro-phenylalanine (4-fluoro-phenylalanine), para-monochloro-phenylalanine (4-chloro-phenylalanine), para-monobromo-phenylalanine (4-bromo-phenylalanine), or penta-fluoro-phenylalanine. In one embodiment, the monomeric insulin analogue has 2-fluoro-phenylalanine at position B24. In another embodiment, the monomeric insulin analogue has a penta-fluoro-phenylalanine at position B24. These halogenated insulin analogues are described, for example, in U.S. Patent Publication Nos. 2011/0166064 and 2014/0128319, the entire contents of which are hereby incorporated by reference.

In some embodiments, the monomeric insulin analogue may include a non-standard amino-acid substitution at position B24. The non-standard amino acid may lack aromaticity. In one example, the non-standard amino acid at position B24 may be cyclohexanylalanine, which includes a nonplanar aliphatic ring system. Loss of planarity in a non-aromatic ring system is associated with a change in its topographical contours and an increase in side-chain volume relative to phenylalanine, which may promote hexamer disassembly.

In other embodiments, the monomeric insulin analogue may include a non-standard amino acid substitution at position B29. In one example, the non-standard amino acid at B29 is norleucine (Nle). In another example, the non-standard amino acid at B29 is ornithine (Orn). Insulin analogs including such non-standard amino acids are described, for example, in U.S. Patent Publication No. 2014/0303076, the entire contents of which are hereby incorporated by reference.

The monomeric insulin analogue may contain other modifications. In various embodiments, the insulin analogue may include one or more mutations at positions corresponding to the following positions of native human insulin: A3, A8, A10, A12, A13, A14, A17, and A21 of the A-chain and B2, B3, B4, B10, B13, B17, B28, and B29 of the B-chain.

In some embodiments, the monomeric insulin analogue contains a substitution of aspartic acid (Asp or D) or lysine (Lys or K) for proline (Pro or P) at amino acid 28 of the B-chain (B28) or a substitution of proline for lysine at amino acid 29 of the B-chain (B29) or a combination thereof. In another example, the monomeric insulin analogue can include a substitution of lysine for asparagine at amino acid 3 of the B-chain (B3) or a substitution of glutamic acid for lysine at amino acid 29 of the B-chain (B29) or a combination thereof.

In some embodiments, the monomeric insulin analogue comprises one or more of the following modifications: lysine, arginine, and leucine at the position corresponding to A3; glutamic acid, histidine, arginine, lysine, and glutamine at the position corresponding to A8; cysteine, glutamic acid, or aspartic acid at position corresponding to A10; aspartic acid or threonine at the position corresponding to A12; tryptophan, tyrosine, histidine, glutamic acid, alanine, or phenylalanine at the position corresponding to A13; histidine or glutamic acid at the position corresponding to A14; tryptophan, tyrosine, alanine, histidine, glutamic acid, glutamine, phenylalanine, or asparagine at the position corresponding to A17; glycine at the position corresponding to A21; cysteine at the position corresponding to B2; lysine at the position corresponding to B3; cysteine at the position corresponding to B4; aspartic acid at the position corresponding to B10; tryptophan, tyrosine, alanine, histidine, glutamic acid, phenylalanine, asparagine, or glutamine at the position corresponding to B13; tryptophan, tyrosine, histidine, or glutamine at the position corresponding to B17; tryptophan, tyrosine, histidine, glutamine, aspartic acid, threonine, alanine, phenylalanine, halogenated phenylalanine (as described above), or cyclohexanylalanine at the position corresponding to B24; and glutamic acid at position B29. In some embodiments, the monomeric insulin analogue includes an aspartic acid at position corresponding to A10 and an ortho-monofluoro-phenylalanine at position corresponding to B24. Exemplary analogs are described, for example, in U.S. Patent Publication No. 2014/0323398, the entire contents of which are hereby incorporated by reference.

In various embodiments, the monomeric insulin analogue may include deletions of one or more amino acids. In an embodiment, the monomeric insulin analogue may include a deletion of amino acids corresponding to positions B1-B3, as described for example, in International Patent Publication No. WO2014/116753, the entire contents of which are hereby incorporated by reference. In some embodiments, the monomeric insulin analogue may include a B chain lacking amino acids B1-B3 in addition to one or more additional substitutions at A8, B24, B28, and/or B29. In an embodiment, the monomeric insulin analogue includes a B chain lacking amino acids B1-B3 and an ornithine or glutamic acid at B29.

In various embodiments, the monomeric insulin analogue may include insertions of one or more amino acids. In an embodiment, the insertions are at the C-terminus. For example, the monomeric insulin analogue may include an addition of at least two amino acids to the carboxyl end of the B-chain. In an embodiment, the B-chain includes a glutamic acid or aspartic acid insertion at position B31 and an additional insertion selected from glutamic acid, alanine, and aspartic acid at position B32. Such insulin analogues are described, for example, in U.S. Pat. No. 8,399,407, the entire contents of which are hereby incorporated by reference. In various embodiments, the monomeric insulin analogue has a B-chain with the amino acid sequence Lys-Pro-Ile-Glu-Glu (KPIEE; SEQ ID NO: 1), Glu-Pro-Ile-Glu-Glu (EPIEE; SEQ ID NO: 2), Pro-Orn-Thr-Glu-Glu (POTEE; SEQ ID NO: 3), or Pro-Orn-Thr-Orn (POTO; SEQ ID NO: 4) at the C-terminus. Such residues respectively comprise residues B28-B32, B28-32, B28-B32, and B28-B31, in which residues B31-B32 are C-terminal extensions of the B chain.

In some embodiments, the monomeric insulin analogue is a single-chain insulin having an insulin A chain and an insulin B chain connected by a linker, as described, for example, in U.S. Pat. Nos. 8,192,957 and 8,501,440, the entire contents of which are hereby incorporated by reference. The linker may be less than 15 amino acids long. For example, the linker may be from 4 to 12 amino acids in length, such as 4, 5, 6, 7, 8, 9, or 10 amino acids in length. In an embodiment, the linker may include the sequence GPRR (SEQ ID NO: 5). In various embodiments, the linker may include the sequence GGGPRR (SEQ ID NO: 6), GGPRR (SEQ ID NO: 7), GSEQRR (SEQ ID NO: 8), RREQKR (SEQ ID NO: 9), RREALQKR (SEQ ID NO: 10), GAGPRR (SEQ ID NO: 11), GGGPGKR (SEQ ID NO: 12), EEGSRRSR (SEQ ID NO: 13), EEGPRR (SEQ ID NO: 14), GEGPRR (SEQ ID NO: 15), AEGSRRSR (SEQ ID NO: 16), ASGSRRSR (SEQ ID NO: 17), EEGSRRD (SEQ ID NO: 18), or EEGSRRK (SEQ ID NO: 19).

In one aspect, the present invention provides monomeric insulin formulations with calcium ion-chelating and/or charge-masking agents. Without wishing to be bound by theory, such agents can mask the charge of the insulin or the surrounding tissue, and/or induce disassembly of adherens junctions and/or tight junctions, to promote rapid insulin absorption. This effect is not related to zinc chelation (and thus hexamer disassembly) because the rapid absorption is observed in the absence of zinc. Without wishing to be bound by theory, it is believed that the calcium ion-chelating agents reduce interstitial calcium ion levels around blood vessels, thereby promoting the disassembly of adherens junctions and tight junctions between endothelial cells of the vessels and enhancing permeability. Alternatively or in addition, and without wishing to be bound by theory, the agents may mask the charges of the tissue surrounding the insulin depot and/or the charges of the insulin molecule itself, thereby mitigating the extent to which a charged monomeric insulin molecule becomes electrostatically bound to the subcutaneous tissue, delaying or preventing its movement to and absorption into vessels.

In an embodiment, the agents include one or more polycarboxylic acid compounds. Exemplary agents include, but are not limited to, ethylenediamine tetraacetic acid (EDTA), ethylene glycol tetraacetic acid (EGTA), and cyclohexane diamino tetraacetic acid (CDTA). In another embodiment, the agent includes one or more anionic polysaccharides. For example, the agent may include alginic acid. In another embodiment, the agent includes one or more organosulfur compounds. For example, the agent may include one or more alpha lipoic acid, dimercaptosuccinic acid (DMSA), dimercaprol, and dimercaptopropane sulfonate (DMPS). In a further embodiment, the agent includes one or more di- or tri-carboxylic acids. These agents include, for example, citric acid or oxalic acid. In a further embodiment, the agents may include one or more benzoates. Agents may be incorporated into the formulation as salts, such as salts comprising one or more of sodium, potassium, and magnesium cations. In another embodiment, the agent includes one or more of penicillamine, and extract or partial extract of chlorella and/or cilantro.

In some embodiments, the calcium ion-chelating and/or charge-masking agent is EDTA and/or EGTA. In certain embodiments, the EDTA and/or EGTA is present in the composition within the range of about 1 to 50 mM, such as within the range of 5 to 25 mM in some embodiments. For example, the composition or formulation may contain about 2 mM EDTA, about 5 mM EDTA, about 10 mM EDTA, about 15 mM EDTA, about 20 mM EDTA, or about 25 mM EDTA. In some embodiments, the composition or formulation may contain about 2 mM EGTA, or about 5 mM EGTA, or about 10 mM EGTA, or about 15 mM EGTA, or about 20 mM EGTA, or about 25 mM EGTA.

In some embodiments, the calcium ion-chelating and/or charge masking agent is citrate or benzoate (e.g., sodium citrate or sodium benzoate). In various embodiments, the citrate or benzoate is present in the formulation at from about 1 mM to about 25 mM, such as from about 5 mM to about 20 mM, or from about 5 mM to about 15 mM, or from about 5 mM to about 10 mM.

In some embodiments, the formulation comprises one or more organic acids having a pKa of from about 3 to about 6. In various embodiments, the acid is not predominately in the protonated form at physiological pH, such that the agent has a net negative charge and has the ability to mask positive charges in the subcutis. Such organic acids may be present in the formulation at from about 1 mM to about 25 mM, such as from about 5 mM to about 20 mM, or from about 5 mM to about 15 mM, or from about 5 mM to about 10 mM.

In some embodiments, the pharmaceutical formulation comprises one or more salts and/or acids sufficient to mask positive charges in the subcutaneous tissue surrounding the insulin depot. For example, the formulation may have an ionic strength equal to or more than that conferred by 0.9% NaCl, or equal to or more than that conferred by 120 mM NaCl. For example, the formulation may have an ionic strength equal to or greater than that conferred by 150 mM NaCl, or 180 mM NaCl, or 200 mM NaCl, or 250 mM NaCl.

In some embodiments, the formulation comprises human C-Peptide. Human C-Peptide carries a net charge of −3 at neutral pH. In some embodiments, the C-Peptide is present at about 5:1 to about 1:5 with respect to the insulin (in moles). In some embodiments, the Human C-Peptide is present at about 2:1 to about 1:2 with respect to insulin, or is present at about equimolar with respect to the insulin.

In still other embodiments, the pharmaceutical formulation comprises one or more molecules with exposed surface charges (e.g., available charges), either positive or negative, sufficient to bind electrostatically or otherwise (and therefore mask from insulin binding) to negatively or positively charged regions on cells, intracellular structures, or interstitial fluid.

The pharmaceutical composition of the present invention can be formulated into any suitable form appropriate for the desired use and route of administration. For example, the pharmaceutical composition can take the form of solutions, suspensions, emulsion, drops, tablets, pills, pellets, capsules, powders, aerosols, sprays, or any other form suitable for administration of insulin, and for which improvements in absorption are desired.

In some embodiments, the pharmaceutical composition is formulated for subcutaneous administration, and may be formulated as an aqueous formulation. However, the formulations of the present invention are applicable to various routes of administration, not limited to parenteral, intradermal, intramuscular, intranasal, sublingual, pulmonary, and oral administration. In an embodiment, the pharmaceutical composition is formulated for subcutaneous administration, and is formulated for delivery using an infusion device, such as an infusion device described herein. Alternatively, the formulation is provided in prefilled insulin pumps or prefilled injection pens and/or single or multiple dose vials or cartridges for subcutaneous administration. For example, the formulation may be provided in vials containing from 1 to 20,000 bolus doses, or from 1 to about 10,000 bolus doses, or from 1 to 5,000 bolus doses, or from 1 to about 1000 bolus doses, or from 1 to about 100 bolus doses, or from 1 to about 50 bolus doses, or from 1 to about 25 bolus doses. In some embodiments, the vial or cartridge is sufficient for providing a daily, weekly, or monthly insulin requirement for a patient. Vials may contain the doses, for example, in about 3 mls to about 50 mls of total volume, such as from about 3 mls to about 10 mls of total volume.

In various embodiments, the pharmaceutical compositions described herein further include one or more pharmaceutically acceptable excipients or carriers, the selection of which will depend on the desired route of administration. Further, a particular excipient may have two or more functions in a formulation. Table 1 below provides a list of exemplary excipients and their exemplary functions in a formulation.

TABLE 1

| | Isotonicity | Preservative | Buffer | Stabilizing | Solubilizing | Anti-aggregation | Trans-membrane | Absorption |
|---|---|---|---|---|---|---|---|---|
| Glycerol | ✓ | | | ✓ | | | | |
| Mannitol | ✓ | | | ✓ | | | | |
| Sorbitol | ✓ | | | ✓ | | | | |
| Propylene glycol | ✓ | | | | | ✓ | | |
| Phenol/m-cresol | | ✓ | | ✓ | | | | |
| TRIS | | | ✓ | ✓ | | | | |
| Arginine | | | ✓ | ✓ | ✓ | ✓ | | |
| Histidine | | | ✓ | ✓ | | ✓ | | |
| Aspartic acid | | | ✓ | | ✓ | | ✓ | |
| Glutamic acid | | | | ✓ | ✓ | | ✓ | |
| Proline | | | | | | ✓ | | |
| Lysine | | | | | | ✓ | | |
| Magnesium | | | | | ✓ | | | ✓ |
| Citrate | | | ✓ | | ✓ | ✓ | ✓ | |
| Nicotinimide | | | | ✓ | | ✓ | | |
| Surfactants | | | | ✓ | | ✓ | | ✓ |
| Alkylglycosides | | | | ✓ | | ✓ | | |

In various embodiments, the pharmaceutical composition includes one or more of a pharmaceutically acceptable buffer, stabilizing agent, surfactant, solubilizing agent, charge-masking agent, anti-aggregation agent, diffusion-enhancing agent, absorption enhancing agent, and preservative. These agents can be used in combination and function synergistically to, for example, enhance insulin absorption, promote a more rapid insulin pharmacokinetics, and increase insulin stability.

In certain embodiments, the pharmaceutical composition may include one or more agents that maintain or adjust the isotonicity of the formulation. Such agents include, but are not limited to, glycerol, mannitol, sorbitol, lactose, dextrose, trehalose, sodium chloride, and propylene glycol (see, for example, U.S. Patent Publication No. 2012/0225810, the entire contents of which are hereby incorporated by reference). In various embodiments, the formulation may be hypertonic or hypotonic. For example, the pharmaceutical composition may contain one or more agents designed to make the formulation hypertonic. Exemplary agents include any agents that are soluble in the formulation and cannot freely permeate the plasma membrane of cells, such as glycerin, dextrose, mannitol, NaCl, and KCl.

In certain embodiments, the pharmaceutical composition may include one or more buffering agents for maintaining a formulation at a specific pH. Exemplary buffering agents include, but are not limited to, sodium phosphate, arginine, TRIS (2-amino-2-hydroxymethyl-1,3-propanediol), glycylglycine, L-Histidine, HEPES, bicine, sodium acetate, sodium carbonate, citrate, sodium dihydrogen phosphate, disodium hydrogen phosphate, bicine, tricine, malic acid, succinate, fumaric acid, tartaric acid, aspartic acid, ethylenediamine or mixtures thereof. See, for example, U.S. Pat. No. 6,906,028 and U.S. Patent Publication No. 2012/0225810, the entire contents of which are hereby incorporated by reference In certain embodiments, the pharmaceutical composition may include one or more stabilizing agents for stabilizing the insulin formulations. Exemplary stabilizing agents include, but are not limited to, zinc (e.g., at a molar ratio less than 0.05 to the insulin in the formulation), phenol, m-cresol, benzoate salts, TRIS, non-reducing carbohydrates (e.g., mannitol or dextran), surfactants (e.g., polysorbates such as TWEEN, bile salts, salts of fatty acids, or phospholipids, partial and fatty acid esters and ethers of polyhydric alcohols, of glycerol or sorbitol and of sucrose, and polyols, partial and fatty acid esters and ethers of polyhydric alcohols such as SPAN polysorbate, MYRJ, BRIJ, TRITON, and CREMOPHOR, poloxyethylene ether, and apolyethylene glycol ether), amino acids (e.g., L-Arginine, L-Glutamic acid, L-histidine, or L-methionine), alkylsaccharides (e.g., dodecyl-(3-D-maltoside, tridecyl maltoside, tetradecyl maltoside, sucrose mono-dodecanoate, sucrose mono-tridecanoate, sucrose mono-tetradecanoate), A-L-S-L-A compounds, chromium salts, acetone, methyl ethyl ketone, propyl methyl ketone, isopropyl methyl ketone, pyruvic acid, glyoxylic acid, alpha-ketobutyric acid, alpha-ketoglutaric acid, acetoacetic acid, pyridoxal, and pyridoxal pyrophosphate, singly or in combination.

In certain embodiments, the pharmaceutical composition may include one or more solubilizing agents to avoid precipitation of the insulin or insulin analogue within a formulation and to enhance solubility of the insulin or insulin analogue. Exemplary solubilizing agents include, but are not limited to, L-Arginine, L-arginine analogues or di- and tri-peptides containing arginine, guanidine, magnesium, alcohols, alcohol esters of organic acids, nitrogen-containing solvents, phospholipids, acetic acid, ascorbic acid, citric acid, glutamic acid, aspartic acid, succinic acid, fumaric acid, maleic acid, adipic acid, agmatine, 4-guanidinobenzoic acid, guanidoacetic acid, guanidinosuccinic acid, and co-polyamino acids, singly or in combination.

In certain embodiments, the pharmaceutical composition may include one or more anti-aggregation agents to avoid insulin aggregation in solution. Exemplary anti-aggregation agents include, but are not limited to, arginine, polysorbate 20, histidine, proline or proline derivatives, sulfobutyl ether-β-cyclodextrin, the tripeptide HTD, argininium ion or lysine, and propylene glycol, citric acid, and nicotinamide.

In certain embodiments, the pharmaceutical composition may include one or more transmembrane agents for facilitating the permeation and diffusion of insulin or an insulin analogue through membranes. Exemplary transmembrane agents include, but are not limited to, acetic acid, ascorbic acid, citric acid, glutamic acid, aspartic acid, succinic acid, fumaric acid, maleic acid, and adipic acid, singly or in combination.

In certain embodiments, the pharmaceutical composition may include one or more absorption enhancing agents for facilitating the absorption of insulin or insulin analogue by any of a variety of mechanisms. Exemplary absorption enhancing agents include, but are not limited to, surfactants (e.g., bile salts, salts of fatty acids, or phospholipids), nicotinic agents (e.g., nicotinamide, nicotinic acid, niacin, niacinamide, vitamin B3 and any salts thereof), pancreatic trypsin inhibitor, magnesium salts, poly-unsaturated fatty acids, didecanoyl phosphatidylcholine, aminopolycarboxylate, tolmetin, sodium caprate, salicylic acid, oleic acid, linoleic acid, EPA, DHA, benzylic acid, NO donors (e.g., 3-(2-Hydroxy-1-(1-methylethyl)-2-nitrosohydrazino)-1-propanamine, N-ethyl-2-(1-ethyl-hydroxy-2-1-nitrosohydrazino)-ethanamine, or S-nitroso-N-acetylpenicillamine), a bile acid, a glycine-conjugated form of a bile acid, sodium ascorbate, potassium ascorbate, sodium salicylate, potassium 5 salicylate, acetyl-salicylic acid, salicylosalicylic acid, aluminum acetylsalicylate, choline salicylate, salicylamide, lysine acetylsalicylate, exalamide, diflunisal, and ethenzamide, singly or in combination.

In certain embodiments, the pharmaceutical composition may include one or more diffusion enhancing agents such as base-substance diffusion enhancing agents. Exemplary diffusion enhancing agents include, but are not limited to, glycosaminoglycanases (e.g., hyaluronidase).

In certain embodiments, the pharmaceutical composition may include one or more preservatives for preventing growth of microorganisms. Exemplary preservatives include, but are not limited to, phenol, meta-cresol, methylparaben, and sodium benzoate.

In various embodiments, the pharmaceutical composition may include one or more vasodilation agents, anti-inflammatory agents, anti-thrombotic agents, anti-degradation agents, insulin-binding antagonist, anti-fibrotic agents, antioxidants, anti-proliferatives, nerve-calming agents, and antibiotics. These agents can be used in combination with any other excipients and agents described herein and may function synergistically to, for example, enhance insulin absorption, promote a more rapid insulin pharmacokinetics, and increase stability of insulin or insulin analogue.

For example, the pharmaceutical composition may include one or more vasodilation agents that increase fluid flow in a region. Exemplary vasodilation agents include, but are not limited to, nitric oxide (NO) donors (e.g., nitroglycerin, isosorbide dinitrate, isosorbide mononitrate, amyl nitrate, erythrityl, tetranitrate, and nitroprusside), histamine, 2-methylhistamine, 2-(2-pyridyl)ethylamine, 2-(2-thiazolyl)ethylamine, 4-methylhistamine, papaverine, minoxidil, dipyridamole, hydralazine, adenosine, GPLC and other embodiments of L-carnitine, arginine, prostaglandin D2, adenosine triphosphate, uridine trisphosphate, potassium salts, and, in certain circumstances, α1 and α2 receptor antagonists (e.g., Prazosin, Phenoxybenzamine, Phentolamine, Dibenamine, and Tolazoline), Betazole, Dimaprit, β2 Receptor Agonists (e.g., Isoproterenol, Dobutamine, Albuterol, Terbutaline, Aminophylline, Theophylline, Caffeine, and Calcium channel blockers (e.g., Amlodipine, Aranidipine, Azelnidipine, Barnidipine, Benidipine, Cilnidipine, Clevidipine, Isradipine, Efonidipine, Felodipine, Lacidipine, Lercanidipine, Manidipine, Nicardipine, Nifedipine, Nilvadipine, Nimodipine, Nisoldipine, Nitrendipine, Prandipine), singly or in combination.

The pharmaceutical composition may include one or more anti-inflammatory agents. Without wishing to be bound by theory, it is believed that the anti-inflammatory agents reduce cellular immune response and consequently, limit the production of oxidative enzymes, certain vasoconstrictive enzymes, cytokines and insulin-degrading proteases near the infusion site, the accumulation of cellular debris, as well as the formation of connective tissue capsules around infusion catheters. Anti-inflammatory agents can also limit down-regulation of eNOS and nNOS, thereby facilitating the maintenance of bioavailable NO with accompanying local vasodilation. Exemplary vasodilation agents include, but are not limited to, thiocarbonates or cryptolepine analogues, immunosuppressants (e.g., cyclosporine, tacrolimus, and sirolimus/rapamycin), toradol, cromolyn sodium, cortisol, methylprednisolone, prednisone, dexamethasone, acetylcysteine, salicylates (e.g., acetylsalicylic acid, diflunisal, salsalate, choline magnesium trisalicylate, sodium salicylate, magnesium salicylate, trolamine salicylate, methyl salicylate), propionic acid derivatives (e.g., ibuprofen, dexibuprofen, naproxen, fenoprofen, ketoprofen, dexketoprofen, flurbiprofen, oxaprozin, loxoprofen), acetic acid derivatives (e.g., indomethacin, tolmetin, sulindac, etodolac, ketorolac, diclofenac, aceclofenac, nabumetone), enolic acid derivatives (e.g., Piroxicam, Meloxicam, Tenoxicam, Droxicam, Lornoxicam, Isoxicam), Fenamic acid derivatives (e.g., Mefenamic acid, Meclofenamic acid, Flufenamic acid, Tolfenamic acid), COX-2 inhibitors (e.g., Celecoxib, Rofecoxib, Valdecoxib, Parecoxib, lumiracoxib, Etoricoxib, Firocoxib), sulphonanilides (e.g., Nimesulide), licofelone, H-harpagide, Lysine clonixinate, doxorubicin, and tamoxifen, singly or in combination.

The pharmaceutical composition may include one or more anti-thrombotic or fibrinolytic agents. Without wishing to be bound by theory, it is believed that anti-thrombotic agents inhibit the coagulation cascade and enhance thrombolysis, thereby reducing thrombus mass that can block fluid flow near any infusion site. Exemplary anti-thrombotic or fibrinolytic agents include, but are not limited to, antithrombins I-III, heparin, warfarin, anisindione, danaparoid, argatroban, lepirudin, bivalirudin, fondaparinux, drotecogin alfa, tissue plasminogen activator (TPa), streptokinase, and urokinase, singly or in combination.

The pharmaceutical composition may include one or more anti-degradation agents. Such agents can reduce insulin degradation in a depot, stabilize insulin's intermolecular bonds, and/or prevent unfolding and amyloidosis of insulin. Exemplary anti-degradation agents include, but are not limited to, aprotinin and human pancreatic trypsin inhibitor, antiretrovirals (e.g., saquinavir, ritonavir, indinavir, nelfinavir, amprenavir, lopinavir, atazanavir, fosamprenavir, tipranavir, and darunavir), velcade, alphal-proteinase inhibitor, doxycycline, Trehalose, L-arginine, L-glycine, L-histidine, glycylglycine, nicotinamide, HP-βCD and cyclodextran derivatives, singly or in combination. In an embodiment, the anti-degradation agent is selected from aprotinin or trehalose.

The pharmaceutical composition may include one or more insulin-binding antagonists. Without wishing to be bound by theory, it is believed that such agents may block potential low-affinity binding sites in subcutaneous tissues which would otherwise slow insulin's diffusion from a depot. Exemplary insulin-binding antagonists include, for example, insulin analogs which have minor modifications to their protein sequence which render them functionally inactive (e.g., Leu-A3 insulin).

The pharmaceutical composition may include one or more charge-masking agents. Without wishing to be bound by theory, it is believed that such agents may block electrostatic binding sites in subcutaneous tissue that would otherwise slow insulin's diffusion from a depot. Exemplary charge-masking agents include, for example, weak or strong acids or bases, and ionic salts.

The pharmaceutical composition may include one or more anti-fibrotic agents. Such agents may block the elaboration of extracellular matrix by fibroblasts. Further still, such agents may block the formation of or enhance the degradation of fibrous capsules around infusion catheters. Exemplary anti-fibrotic agents include, but are not limited to, matrix metalloproteinases (e.g., collagenase-1-3 and -4, gelatinase A and B, stromelysin-1, -2 and -3, transin-1, matrilysin, elastase and others), tamoxifen, fibrinolytic agents such as fibrinolysin, tissue plasminogen activators (e.g., alteplase, retaplase and tenecteplase), streptokinase (e.g., natural streptokinase and anistreplase) and urokinase (e.g., Abbokinase®).

The pharmaceutical composition may include one or more anti-oxidants. Such agents may counter the pro-inflammatory and/or insulin-degrading effects of oxygen-derived free radicals generated by oxidative enzymes. Exemplary anti-oxidants include, but are not limited to, GPLC (glycine propionyl-l-carnitine), acetylcarnitine, L-carnitine and other entities comprising L-cartinine, Pentoxifylline, Ascorbic acid, Retinol, Ubiquinone, Melatonin, glutathione and respective derivatives and Alpha Lipoic Acid. In an embodiment, the anti-oxidant is selected from GPLC (Glycine propionyl-l-carnitine), acetylcarnitine, L-carnitine, or other L-cartinine containing compounds, Ascorbic acid, Melatonin, or glutathione and respective derivatives, singly or in combination.

The pharmaceutical composition may include one or more anti-proliferatives. Without wishing to be bound by theory, it is believed that anti-proliferatives may prevent local proliferation of leukocytes, smooth muscle cells, fibroblasts and other immune or repair cells, thereby, reducing the number of cells that would otherwise be in the area of an infusion-catheter-related injury where such cells would, among other things, excrete extracellular matrix that could obstruct blood vessel or interstitial fluid flow and/or contribute to encapsulation of the catheter tip. Exemplary anti-proliferatives include, for example, plavopiridol and paclitaxel.

The pharmaceutical composition may include one or more nerve-calming agents that reduce local nerve signaling that may otherwise present as a local site reaction. Exemplary nerve-calming agents include, but are not limited to, magnesium sulfate, Lidocaine, Bupivicaine, Etidocaine, Isoflurane, Halothane, Sevoflurane, Desflurane, Enflurane, procaine, benzocaine, chloroprocaine, cocaine, cyclomethycaine, dimethocaine/larocaine, piperocaine, propoxycaine, procaine/novocaine, proparacaine, tetracaine/amethocaine, articaine, cinchocaine/dibucaine, levobupivacaine, lignocaine, mepivacaine, prilocaine, ropivacaine, trimecaine, saxitoxin, neosaxitoxin, tetrodotoxin, menthol, eugenol, and post ganglionic adrenergic blockade agents (e.g., guanethidine and bretylium), singly or in combination. In an embodiment, the nerve-calming agent is magnesium sulfate, Lidocaine, Bupivacaine, or ropivacaine.

The pharmaceutical composition may further include one or more antibiotics. Exemplary antibiotics include, but are not limited to, preservatives (included at higher than normal levels), amikacin, gentamicin, kanamycin, neomycin, netilmicin, tobramycin, paromomycin, spectinomycin, geldanamycin, herbimycin, rifaximin, streptomycin, loracarbef, ertapenem, doripenem, imipenem/cilastatin, meropenem, cefadroxil, cefazolin, cefalotin or cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, temocillin, ticarcillin, amoxicillin/clavulanate, ampicillin/sulbactam, piperacillin/tazobactam, ticarcillin/clavulanate, bacitracin, colistin, polymyxin b, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide (archaic), sulfasalazine, sulfisoxazole, trimethoprim-sulfamethoxazole(co-trimoxazole) (tmp-smx), sulfonamidochrysoidine(archaic), demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, and trimethoprim, singly or on combination.

In various embodiments, the pharmaceutical composition may also include one or more peptide agents that open tight junctions, for example, for pulmonary and intestinal applications. Such peptide agents include, but are not limited to, zonula occludens toxin (ZOT), zonulin, or the peptide FCIGRL (see, for example, U.S. Patent Publication Nos. 2008/0014218 and 2007/0196272, and U.S. Pat. Nos. 8,557,763 and 8,728,491, the entire contents of all of which are incorporated herein by reference).

In various embodiments, the pharmaceutical composition of the present invention may include any of the agents described herein at a concentration well below the minimum systemic effect level. In some embodiments, the combination of one or more agents described herein has synergistic effects in, for example, enhancing insulin absorption, promoting a more rapid insulin pharmacokinetics, and increasing insulin stability. Table 2 below lists exemplary dosing ranges for some of the agents.

TABLE 2

| Agent | Systemic Dose Range | Excipient Dose Range |
|---|---|---|
| Prazosin | 0.5-40 mg/day | 0.09-144 µg/day |
| Phenoxybenzamine | 20-120 mg/day | 1-120 µg/day |
| Phentolamine | 5 mg/day | 1-20 µg/day |
| Dibenamine | 161-420 mg/day | 32.2-1680 µg/day |
| Tolazoline | 40-200 mg/day | 8-800 µg/day |
| Chlorpromazine | 30-400 mg/day | 1.92-51.2 µg/day |
| Haloperidol | 1-15 mg/day | 0.12-36 µg/day |
| Papaverine HCl | 30-960 mg/day | 6 to 3840 µg/day |
| Sodium nitroprusside | 210-7000 µg/day | 0.042-28 µg/day |
| KCl | up to 29.8 g/day | 2.98-59.6 mg/day |

TABLE 2-continued

| Agent | Systemic Dose Range | Excipient Dose Range |
|---|---|---|
| ATP | up to 5.04 g/day | 1.008-20.16 mg/day |
| PGD2 (prostaglandin D2) | up to 51.6 mg/day | 10.32-206.4 μg/day |
| Isosorbide dinitrate | 40-60 mg/day | 6-120 μg/day |
| Isosorbide mononitrate | 20-60 mg/day | 4 to 240 μg/day |
| L-arginine | 30 g/day | 6-120 mg/day |
| Hydralazine | 200-300 mg/day | 15.2-456 μg/day |
| Adenosine | 6-30 mg/day | 1.2-6 μg/day |
| Dipyridamole | 300-400 mg/day | 12-240 μg/day |
| Diazoxide | 210-1050 mg/day | 42-4200 μg/day |
| Minoxidil | 5-40 mg/day | 0.9-360 μg/day |
| Histamine | 1.925-2.8 mg/day | 0.385-11.2 μg/day |
| Bradykinin | 30-90 mg/day | 5.82-349.2 μg/day |
| GPLC (Glycine propionyl-l-carnitine) | 1500 mg/day | 48-960 μg/day |
| Nitroglycerine | 0.4-1.2 mg/day | 0.0308-1.848 μg/day |
| Erythrityl tetranitrate | 30-50 mg/day | 6-200 μg/day |
| Isoproterenol | 0.02-0.26 mg/day | 0.004-1.04 μg/day |
| Dobutamine | 50.4-4032 mg/day | 10.08-16128 μg/day |
| Albuterol | 6-32 mg/day | 8-86.4 μg/day |
| Terbutaline | 0.25-3 mg/day | 0.05-12 μg/day |
| Aminophylline | up to 1125 mg/day | 0.225-4.5 mg/day |
| Theophylline | up to 900 mg/day | 0.18-3.6 mg/day |
| Caffeine | 65-1200 mg/day | 13-4800 μg/day |
| Amlodipine | 5-10 mg/day | 0.77-30.8 μg/day |
| Aranidipine | 5-20 mg/day | 0.18-14.4 μg/day |
| Azelnidipine | 8-16 mg/day | 0.288-5.76 μg/day |
| Barnidipine | 5-20 mg/day | 0.145-11.6 μg/day |
| Benidipine | 2-8 mg/day | 0.072-5.76 μg/day |
| Cilnidipine | 5-20 mg/day | 0.18-14.4 μg/day |
| Clevidipine | 24-504 mg/day | 4.8-2016 μg/day |
| Isradipine | 5 to 20 mg/day | 1 to 74 μg/day |
| Efonidipine | 20-60 mg/day | 0.72-43.2 μg/day |
| Felodipine | 2.5-10 mg/day | 0.0825-6.6 μg/day |
| Lacidipine | 2-8 mg/day | 0.074-5.92 μg/day |
| Lercanidipine | 10-30 mg/day | 0.2-12 μg/day |
| Manidipine | 10-20 mg/day | 0.96-38.4 μg/day |
| Nicardipine | 60-120 mg/day | 4.2-168 μg/day |
| Nifedipine | 30-60 mg/day | 2.7-108 μg/day |
| Nilvadipine | 8-16 mg/day | 0.264-10.56 μg/day |
| Nimodipine | 360 mg/day | 9.36-187.2 μg/day |
| Nisoldipine | 17-34 mg/day | 0.17-6.8 μg/day |
| Nitrendipine | 10-80 mg/day | 0.46-73.6 μg/day |
| Pranidipine | 1-4 mg/day | 0.036-2.88 μg/day |
| Guanethidine | 10-100 mg/day | 0.53-106 μg/day |
| Bretylium | 350-700 mg/day | 210-11200 μg/day |
| DMSO | 7-15 g/day | 1.4-104 mg/day |
| Mannitol | 50-200 g/day | 10-800 mg/day |
| Albumin | 1.75-3.5 g/day | 0.35-14 mg/day |
| Tamoxifen | 20 mg/day | 4-80 μg/day |
| Polysorbate 80 | n/a | 0.005-1672 μg/day |
| Polysorbate 20 | n/a | .002-224 μg/day |
| Streptokinase | 1500000 IU/day | 300-6000 IU/day |
| Streptodornase | n/a | 25-500 U/day |
| Urokinase | 308000 IU/day | 61-1232 IU/day |
| rtPA | 15-90 mg/day | 3-360 μg/day |
| Hyaluronidase | | 300 U/ml |
| Acetylcysteine | 10.5 g/day | 2.1-42 mg/day |
| Dnase | 2.5 mg/day | 0.075-1.5 μg/day |
| Chymotrypsin | | |
| Collagenase | 2.32 mg/ml | 0.46-9.28 μg/ml |
| Fibrinolysin | 2.5 mg/ml | .5-10 μg/ml |
| MMPs | | |
| Heparin | 5,000-20,000 u | 1-80 u |
| Dexamethasone | 0.5-9 mg/day | 0.1-36 μg/day |
| Cortisol | 100-500 mg/day | 20-2000 μg/day |
| Solumedrol | 10-40 mg | 2-160 μg/day |
| Medrol | 4-48 mg/day | 0.72-172 μg/day |
| Lidocaine | 50-100 mg | 10-400 μg |
| Bupivicaine | 7.5-10.5 mg | 1.5-42 μg |
| Procaine | 50-100 mg | 10-400 μg/day |
| Etidocaine | 560 mg/day | 0.112-2.24 mg/day |
| Ropivican | 5-200 mg | 1-800 μg/day |
| Mepivican | 400 mg-1000 mg/day | 80-4000 μg/day |
| Aprotinin | 10,000-500,000 KIU/day | 2-2000 KIU/day |
| Acetylsalicytic Acid | 1-3 g/day | 0.2-12 mg/day |
| Nicotinamide | 0.05-500 mg/day | 0.01-2000 μg/day |
| Toradol | 3-120 mg/day | 6-480 μg/day |
| Sodium Salicylate | 560 mg/day | 0.112-2.24 mg/day |

TABLE 2-continued

| Agent | Systemic Dose Range | Excipient Dose Range |
|---|---|---|
| Magnesium salicylate | 460-3600 mg/day | 0.092-14.4 mg/day |
| Trolamine salicylate | | |
| Methyl salicylate | | |
| Cromolyn Sodium | 800-2800 mg/day | 1.6-112 μg/day |
| Ciclosporin | 3-10 mg/day | 0.042-2.8 mg/day |
| Tacrolimus | 700-3500 μg/day | 0.14-14 μg/day |
| Sirolimus (rapamycin) | 2 mg/day | 0.06-1.2 μg/day |
| GPLC (Glycine propionyl-l-carnitine) | 1500 mg/day | 0.3-6 mg/day |
| Pentoxyphilline | 1200 mg/day | 0.24-4.8 mg/day |
| Ascorbic acid | 0.1-2 g/day | 0.2-8 mg/day |
| Retinol | 700 to 900 μg/day | 0.112-2.88 μg/day |
| Ubiquinone | 1200 mg/day | 240-4800 μg/day |
| Melatonin | 2 mg/day | 0.2-4 μg/day |
| Alpha Lipoic Acid, | 600-1200 mg/day | 0.12-4.8 mg/day |
| Paclitaxel (Taxol) | 135 mg/m$^2$ | 0.027-0.54 mg/m$^2$ |

In various embodiments, the pharmaceutical composition does not include zinc, or contains less than 0.05 moles of zinc per mole of insulin.

It will be appreciated that the actual dose of the insulin or monomeric insulin analogue or dimeric insulin analogue to be administered according to the present invention will vary according to, for example, the particular dosage form and the mode of administration, as well as the patient's disease.

Individual doses of the insulin or monomeric insulin analogue or dimeric insulin analogue can be formulated at, for example, about 1 U/ml (1 insulin unit per ml) to about 2000 U/ml, or about 1 U/ml to about 1000 U/ml, or about 1 U/ml to about 500 U/ml, or about 1 U/ml to about 400 U/ml, or about 1 U/ml to about 300 U/ml, or about 1 U/ml to about 200 U/ml, or about 1 U/ml to about 100 U/ml, or about 1 U/ml to about 50 U/ml, or about 1 U/ml to about 10 U/ml. In some embodiments, the formulation contains from 1 U to about 100 U per bolus administration, such as about 1 U to about 20 U in some embodiments (e.g., about 5 U, about 10 U, about 12 U, or about 15 U).

In various embodiments, the pharmaceutical composition of the present invention provides an onset of insulin activity (e.g., which can be measured as $\frac{1}{2}$ $T_{max}$—early) of less than about 40 minutes after administration, or less than about 30 minutes, or less than about 20 minutes, or less than about 15 minutes, or less than about 10 minutes, or less than about 5 minutes after administration in various embodiments.

In various embodiments, the pharmaceutical composition provides a rapid insulin absorption profile as measured by, for example, $C_{max}$ and/or $T_{max}$. As used herein, $C_{max}$ is the maximum or peak concentration of a drug observed after its administration. As used herein, $T_{max}$ is the time at which maximum concentration ($C_{max}$) occurs. In certain embodiments, the pharmaceutical composition reaches a $T_{max}$ at less than about 120 minutes, or less than about 90 minutes, or less than about 60 minutes, or less than about 50 minutes, or less than about 40 minutes, or less than about 30 minutes, or less than about 20 minutes, or less than about 15 minutes after administration.

In various embodiments, the pharmaceutical composition provides a short duration of insulin activity. In certain embodiments, the pharmaceutical composition provides a duration of insulin activity of about 5 hours or less, about 4 hours or less, about 3 hours or less, or about 2 hours or less after administration. In a further embodiment, the pharmaceutical composition provides a duration of insulin activity of from about 1 to 2 hours after administration. In some embodiments, duration of activity is measured as the time to which insulin action subsides to less than $\frac{1}{2}$ maximal activity.

In exemplary embodiments, the pharmaceutical composition upon subcutaneous injection provides an onset of insulin activity (e.g., measured as $\frac{1}{2}$ $T_{max}$) in about 30 minutes or less or in about 20 minutes or less, with a duration of activity of about 2 hours or less.

In various embodiments, the pharmaceutical composition provides enhanced storage stability. In certain embodiments, the pharmaceutical composition is stable for at least about 1 month, or at least about 3 months, or at least about 6 months, or at least about 12 months, or at least about 18 months, or longer, at 25° C. without substantial formation of insulin fibrils.

In further embodiments, the pharmaceutical composition maintains at least about 60% potency, about 70% potency, about 80% potency, about 90% potency, or about 95% potency after six months at 25° C. In another embodiment, the pharmaceutical composition maintains at least about 60% potency, about 70% potency, about 80% potency, about 90% potency, or about 95% potency after 9 months at 30° C. In a further embodiment, the pharmaceutical composition maintains at least about 60% potency, about 70% potency, about 80% potency, about 90% potency, or about 95% potency after 12 months at 25° C.

In one aspect, the present invention provides devices that enable the infusion of pharmaceutical formulations, including insulin or insulin analogues, or other pharmaceuticals, such that the infusion exhibits enhanced pharmaceutical properties such as more rapid pharmacokinetics (e.g., rapid onset of action, and/or shorter duration). In an embodiment, the present invention provides devices that enhance the subcutaneous infusion and absorption of pharmaceutical formulations such as insulin or insulin analogues into the circulation from a subcutaneous depot. Without wishing to be bound by theory, it is believed that the infusion devices of the present invention enhance active agent diffusion from the injection depot to both blood and lymphatic vessels and increase the rate at which the active agent is absorbed into these vessels. In some embodiments, the invention improves the uptake of active agent by blood vessels as opposed to lymphatic vessels.

In various embodiments, the present invention provides an infusion set for use with pharmaceutical formulations, and one or more energy delivery systems, such as an ultrasound transducer, a tactor, and/or an electrophoresis electrode. In some embodiments, the pharmaceutical formulation is an insulin formulation, which may include any insulin or insulin analogue known in the art and/or as described herein. In an embodiment, the insulin formulation for use with the infusion set exhibits rapid hexamer disassembly, as compared to native human insulin. In another embodiment, the insulin formulation is a substantially zinc-free formulation of a stable monomeric or dimeric insulin analogue formulation. In a further embodiment, the insulin formulation includes any of the insulin pharmaceutical compositions as described herein.

In some embodiments, the agent is a protein, peptide, oligonucleotide, or small molecule active agent that is not rapidly absorbed upon subcutaneous injection. In some embodiments, the active agent is an antibody or antigen-binding portion thereof, or is a cytokine or growth factor. In some embodiments, such as those that employ electrophoresis in the infusion set, the active agent has a net negative charge of at least −2 or a net positive charge of at least +2.

In various embodiments, the infusion set includes a first body, an adhesive surface, a subcutaneous infusion catheter, and one or more energy delivery systems selected from an ultrasound transducer, a tactor, and an electrophoresis electrode. The infusion set may include additional companion devices that enable the easy placement or insertion of the infusion catheter into the skin.

In various embodiments, the infusion set includes a first body to which other pieces may be connected. In an embodiment, the body is made up of a plastic, such as a semi-rigid plastic.

In various embodiments, infusion set includes an adhesive surface. The adhesive surface holds the infusion set onto the surface of the skin.

In various embodiments, the infusion set includes a catheter. More specifically, the infusion set includes a subcutaneous infusion catheter. In an embodiment, the catheter runs from the first body through the plane of the adhesive surface, through the dermis, and into the subcutis. In an embodiment, the catheter projects about 1 mm to about 10 mm into the subcutis. For example, the catheter may project about 3 mm, about 5 mm, about 6 mm, about 7 mm, about 8 mm, about 9 mm, or about 10 mm into the subcutis. In an embodiment, the catheter projects about 7 mm into the subcutis. The catheter can be made of various materials, including but not limited to Teflon or metal.

The infusion set may further include a supply tube or a port to which a supply tube can be connected. The supply tube, when connected, is in continuous fluid communication with the infusion catheter such that the active agent (e.g., insulin) can be pumped through the supply tube into the catheter. In various embodiments, an active agent reservoir can be connected and disconnected to the supply tube.

In certain embodiments, infusion set is operably connected to a pump and a controller operably connected to an active agent (e.g., insulin) reservoir for delivering active agent through the supply tube to the catheter. The pump includes a pumping mechanism such as a step, electromechanical, electrochemical, chemical, or other motor that drives a rotary piston, a compression bladder, syringe, or other mechanism. The controller typically contains a microprocessor, a control algorithm, and an interface display, which are optionally contained in the first body. The controller may further include one or more external user controls and/or a communication interface, which are optionally contained in the first body. For example, the controller may include one or more input controls such as buttons, optionally an external input port, optionally a wireless communications interface, and one or more actuator interfaces designed to drive the pumping mechanism and possibly other devices.

In certain embodiments, the reservoir is included in a second body which can be detached from the first body. In such embodiments, an adhesive surface may be located on the second body. In an embodiment, the second body also includes the infusion catheter. The second body can be replaced from time to time as active agent needs replenishing.

Figure 7A:
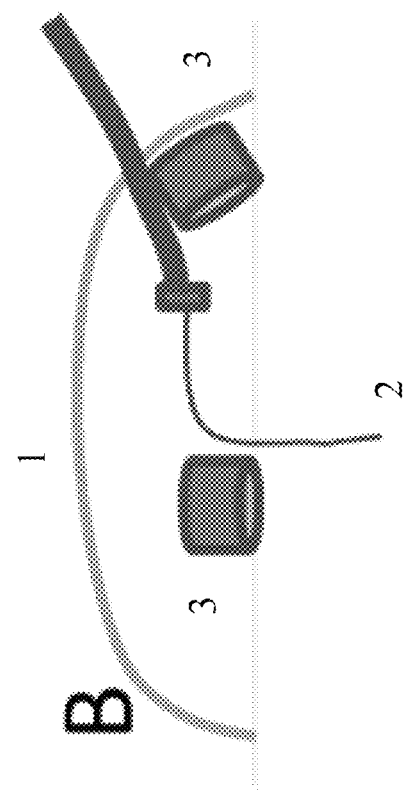
FIG. 7A shows a schematic of the top view of a prototype infusion set head.
Figure 7B:
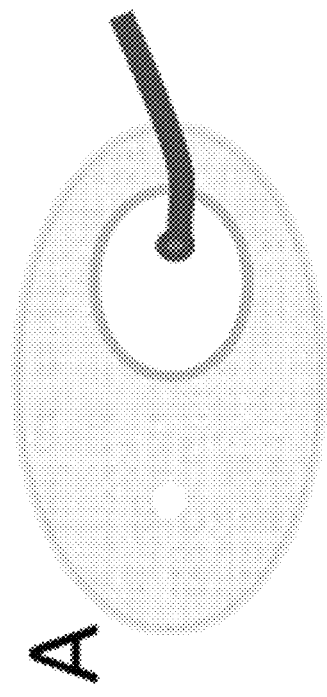
FIG. 7B shows a schematic of the side view of a prototype infusion set head with possible locations of ultrasound Transducers (3).

In some embodiments, the infusion set comprises an ultrasound transducer. In some embodiments, the ultrasound transducer is a low intensity ultrasound (LITUS) transducer. In other embodiments, the infusion set comprises a tactor, such as a low-frequency piezoelectric tactor. In some embodiments, the transducer or the tactor is positioned above the distal end of the infusion catheter. In other embodiments, the transducer or the tactor is placed at some other location within the body of the infusion set. In some embodiments, the transducer or the tactor is contained within the first body. For example, the body of the infusion set may have a first body (1) which contains the transducer or the tactor (3) and a second body that is connected to the adhesive surface and infusion catheter (2). FIGS. 7A and 7B.

In various embodiments, the transducer or the tactor are energy efficient, using for example, about 1 μW, about 10 μW, about 0.1 mW, or about 1 mW, or about 10 mW of power. For example, the transducer or the tactor may be powered by a battery that powers the pump. Optionally, the transducer or the tactor are driven by a signal generator in the pump, which is controlled by the pump. Alternatively, the transducer or the tactor are powered by a rechargeable battery in the infusion set itself, are driven by a signal generator in the infusion set itself, and/or are controlled by a switch on the infusion set or by wired or wireless remote control (for example, over Bluetooth, Zigbee, or other wireless protocols).

In some embodiments, the ultrasound transducer emits a signal within the range of about 0.1 MHz to about 5 MHz, about 0.2 to about 3 MHz, about 0.2 to about 2.5 MHz, about 0.2 to about 2 MHz, about 0.2 to about 1.5 MHz, about 0.2 to about 1 MHz, about 0.2 to about 0.5 MHz, about 0.5 to about 3 MHz, about 0.5 to about 2.5 MHz, about 0.5 to about 2 MHz, about 0.5 to about 1.5 MHz, about 0.5 to about 1 MHz, about 1 MHz to about 2 MHz, or about 1 MHz to about 1.5 MHz, inclusive of all values and ranges therebetween. For example, the ultrasound transducer may emit a signal of about 0.1 MHz, about 0.2 MHz, about 0.3 MHz, about 0.4 MHz, about 0.5 MHz, about 0.6 MHz, about 0.7 MHz, about 0.8 MHz, about 0.9 MHz, about 1.0 MHz, about 1.5 MHz, about 2.0 MHz, about 2.5 MHz, about 3.0 MHz, about 3.5 MHz, about 4.0 MHz, about 4.5 MHz, or about 5.0 MHz, inclusive of all values and ranges therebetween.

In some embodiments, the piezoelectric tactor emits a signal with a frequency of less than about 2 kHz, or less than about 1 kHz, such as from about 0.1 kHz to about 1.0 kHz. In an embodiment, the piezoelectric tactor emits a signal with a frequency of less than about 1 kHz. Without wishing to be bound by theory, it is believed that such a low-frequency tactor can reproduce the effects of vibrational massage on an infusion site.

Different frequencies resonate with different tissues (for example, 1 $mm^2$ fat lobules may have a characteristic frequency of about 170 kHz). Accordingly, in an embodiment, the transducers may be driven at a variety of frequencies and in different patterns. In an embodiment, the transducer or the tactor produces square waves, which produce multiple harmonics. In another embodiment, the transducer or the tactor produces a saw tooth wave or other forms which may have more motive effect. In various embodiments, the transducer or the tactor may deliver a signal continuously. In other embodiments, the transducer or the tactor may deliver a pulsed signal (for example, 10% off and 90% on; 20% off and 80% on; 30% off and 70% on; 40% off and 60% on; or 50% on and 50% off), which may be more effective in relatively static tissues. In various embodiments, the transducer or the tactor operates at a low power level, a moderate power level, or at a high power level.

The ultrasound or tactor may operate before, during, and/or after insulin infusion.

In various embodiments, the adhesive surface is ultrasonically transmissive, particularly in embodiments where an ultrasound is positioned in the first body above the second body that contains the insulin reservoir and adhesive surface.

In some embodiments, the infusion set comprises an electrophoresis electrode. As demonstrated herein, applying an electric field to an insulin depot can cause the insulin to migrate through a gel at a rate of between 1 and 2 mm/min, depending on the charge of the insulin. Without wishing to be bound by theory, it is believed the electric field can draw insulin up towards the deep vascular plexus in the dermis just above the subcutis where the insulin can be more rapidly absorbed. In various embodiments, the infusion set can draw insulin to the capillary rich vascular plexus in 5 minutes or less when the distal end of the infusion set of less than 6 mm below the dermis.

Figure 8C:
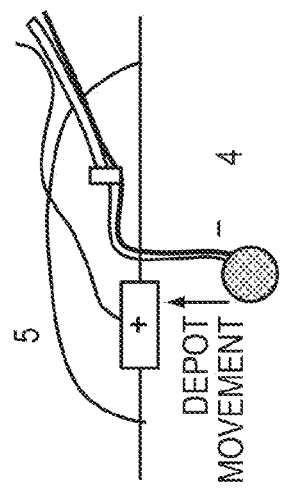
FIGS. 8A-8C show schematics of electrophoresis infusion sets.
Figure 8B:
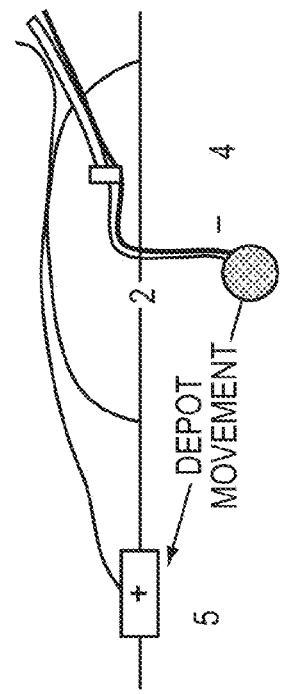
Figure 8A:
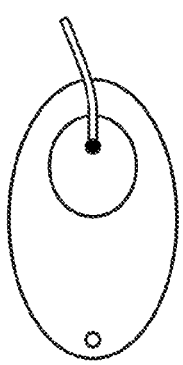

In an embodiment, and as shown in FIGS. 8A and 8B, the infusion set may comprise at least two electrophoresis electrodes. In an embodiment, the first electrophoresis electrode (4) is proximal to the distal end of the infusion catheter. In some embodiments, the first electrophoresis electrode is connected to the voltage source partly by one or more conductive metal or plastic wires imbedded in or attached to the inner or outer surface of the infusion catheter lumen. In some embodiments, the entire infusion catheter lumen is conductive or is comprised of a conductive lumen coated on one or more surfaces with an insulating film or by an insulating lumen. In some embodiments, the electrode on the distal end is at least 1 mm long and may encompass the entire circumference of the lumen. Alternatively, there may be multiple infusion catheter electrodes placed along the infusion catheter. In one embodiment, the infusion catheter lumen may be perforated along its length to allow the infusate to escape from the lumen other than from the distal end.

Figure 9A:
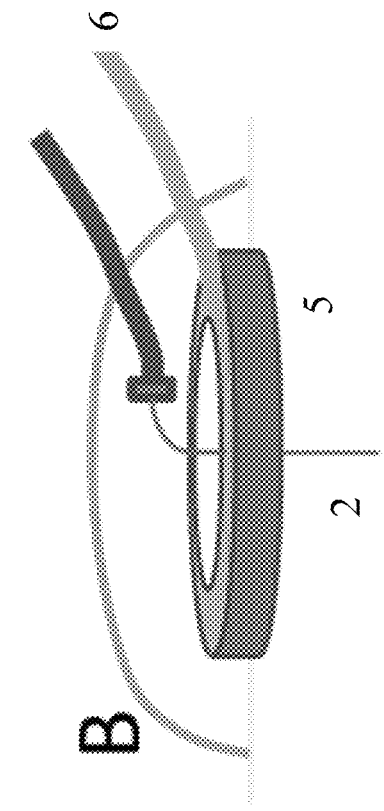
FIGS. 9A and 9B show the top and side views, respectively, of a schematic of a skin surface electrode in ring shape.
Figure 9B:
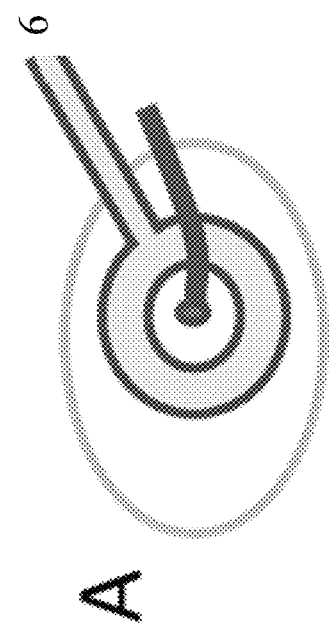
Figure 10:
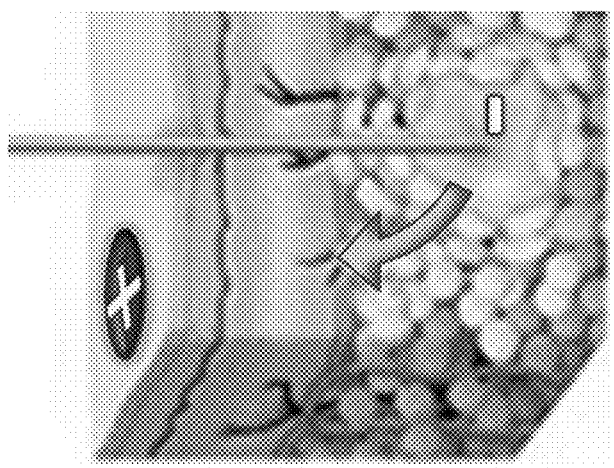
FIG. 10 shows how negatively charged insulin depot migrates rapidly to the lower dermis under electromotive force (EMF).
Figure 11:
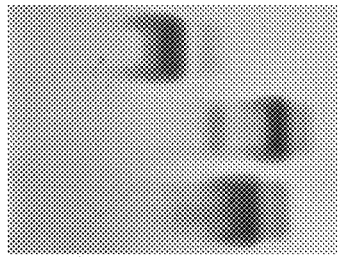
FIGS. 11A and 11B demonstrate that insulin and various analogs of insulin migrate in gradient acrylamide gel at pH 7 @ 0.5 mA/cm for 15 m.

In an embodiment, the second electrophoresis electrode (5) is on the skin surface. Optionally, the second electrophoresis electrode is attached to the adhesive surface. FIG. 8C. The second electrophoresis electrode may have a coating designed to increase conductivity to the skin such as a biocompatible, electrochemical gel or adhesive. In an embodiment, the second electrophoresis electrode may be positioned above the distal end of the infusion catheter. FIG. 8C. In another embodiment, the skin-surface second electrophoresis electrode forms a pattern, such as a ring or a square or a series of discontinuous shapes around the point where the infusion catheter enters the dermis (FIG. 9). In another embodiment, the skin-surface second electrophoresis electrode is located some distance from the infusion catheter. In another embodiment, all or part of the adhesive surface is electrically conductive and serves as an electrode. In an alternate embodiment, the skin-surface electrode is above the skin surface and not in direct contact with the skin.

In various embodiments, the first and second electrophoresis electrodes are connected to opposite ends of a voltage source (6). In an embodiment, the first electrophoresis electrode is a cathode and the second electrophoresis electrode is an anode. In other embodiments, the first electrophoresis electrode is an anode and the second electrophoresis electrode is a cathode. The actual selection will be based on, for example, the charge of the active agent. In an embodiment, the electrodes are connected by an electrical conductor to an interface plug designed for easy connection or disconnection to or from the voltage source. In various embodiments, the voltage source provides a constant voltage. The voltage may be in the range of about 0.1 volt to about 20 volts, about 0.1 volt to about 19 volts, about 0.1 volt to about 18 volts, about 0.1 volt to about 17 volts, about 0.1 volt to about 16 volts, about 0.1 volt to about 15 volts, about 0.1 volt to about 14 volts, about 0.1 volt to about 13 volts, about 0.1 volt to about 12 volts, about 0.1 volt to about 11 volts, about 0.1 volt to about 10 volts, about 0.1 volt to about 9 volts, about 0.1 volt to about 8 volts, about 0.1 volt to about 7 volts, about 0.1 volt to about 6 volts, about 0.1 volt to about 5 volts, about 0.1 volt to about 4 volts, about 0.1 volt to about 3 volts, or about 0.1 volt to about 2 volts, inclusive of all values and ranges therebetween. In an embodiment, the voltage is in the range of about 1 volt to about 15 volts or about 1 volt to about 10 volts. In an embodiment, the voltage is about 1 volt, about 2 volts, about 3 volts, about 4 volts, about 5 volts, about 6 volts, about 7 volts, about 8 volts, about 9 volts, about 10 volts, about 11 volts, about 12 volts, about 13 volts, about 14 volts, about 15 volts, about 16 volts, about 17 volts, about 18 volts, about 19 volts, or about 20 volts, inclusive of all values and ranges therebetween.

In an embodiment, the voltage source is powered by the battery in the insulin pump and controlled by the pump. In this embodiment, the voltage source is connected to the infusion set by wires that run along or are imbedded in the insulin supply tube. In alternate embodiments, the voltage source is powered by a rechargeable battery in the infusion set itself and/or is controlled by a switch on the infusion set or by wired or wireless remote control (for example, over Bluetooth, Zigbee, WiFi, or other wireless protocols). In one embodiment, the voltage source and controller is contained in a second, reusable body which fits together with a first, disposable body which is connected to the adhesive surface, infusion catheter, and electrodes and which has an interface mechanism to ensure proper connection between the lumens and wires of the first and second bodies.

In an embodiment, voltage can be turned on just before or at the time of bolus infusion and be turned off manually or under timed or remote control after 0.5, 1, 1.5 or 2 hours or some other amount of time. In a preferred embodiment, this on-off control would be controlled by the pump, either directly through an actuator interface or indirectly through a wireless connection.

In an embodiment, the voltage source negative terminal is connected to the first electrophoresis electrode. In an embodiment, the voltage applied is regulated so as to produce between about 0.2 and about 5.0 mA of current.

The electrophoresis electrodes can be made of any conductive material or material doped to be conductive. In an embodiment, the electrophoresis electrodes include a conductive coating. The conductive coating may further include a material with anti-microbial characteristics. In an embodiment, the conductive coating may include a silver-containing compound with anti-microbial characteristics. Further still, it has been discovered that the electric field generated by the current between the electrophoresis electrodes of the present invention has antifouling and antimicrobial effects. Thus, in one embodiment, the electric current between the electrodes is sufficient to create a bioelectric effect.

In various embodiments where an electrode is contained in the first body above the second body having the adhesive surface, the second body and the adhesive surface are electrically conductive.

In an embodiment, the infusion set of the present invention further includes an insulin reservoir. In a still further embodiment, the infusion set of the present invention further includes a catheter insertion device. In an alternate embodiment, the first electrophoresis electrode can be positioned proximal to, positioned distant from, or integrated with a sensor, such as a glucose sensor, which is also resident on the infusion catheter. In another embodiment, the electrode can extend beyond the end of the infusion catheter lumen or be mounted on a component that extends beyond the end of the lumen. In an alternate embodiment, the infusion catheter could be replaced or supplemented by an electrophoresis electrode placed separately from the infusion catheter into the subcutaneous tissue.

In various embodiments, the ultrasound transducer, tactor, or electrophoresis system may be used to enhance the absorption of rapid-acting insulin, or basal insulin, or both.

In various embodiments, the various components of the infusion set as described herein have synergistic effects in, for example, facilitating insulin absorption and promoting a more rapid insulin pharmacokinetics. For example, the insulin infusion set of the invention may include a combination of an ultrasound transducer, a tactor, and/or an electrophoresis electrode, which produce synergistic effects in, for example, enhancing insulin absorption.

One of the challenges associated with the use of infusion sets and infusion catheters is maintaining long-term patency. Currently, the FDA requires that infusion sets be replaced every 2-3 days. This is because of the risks of catheter occlusion due to the presence of fibrous capsules generated by the body's immune response. The fibrotic capsules may impede the diffusion of insulin and or the flow of infusate. Further still, inflammatory cascades and the corresponding cellular immune response, triggered by tissue damage and wounds caused by catheter placement and post-placement movement can lead to the accumulation of cellular debris around the catheter and impede the flow of insulin from the catheter. Further still, the risks for infection around the area of catheter placement also increase with time of use. In addition to enhancing absorption of insulin, in some embodiments the invention also provides for infusion sets that last longer than 3 days, such as at least about 5 days, or at least about 1 week, or at least about 2 weeks, or at least about 1 month.

Accordingly, in various embodiments, the pharmaceutical composition of the present invention restricts the clotting cascade to mitigate the formation of thrombus, limits the cellular immune response, and reduces fibrosis resulting in enhanced catheter patency. The pharmaceutical composition of the present invention also impedes the growth of microorganisms such as bacteria and fungi in the catheter placement wound so as to reduce infection. For example, the pharmaceutical composition of the present invention reduces the burning, irritation, and inflammation around the site of catheter placement.

Specifically, various agents may be added to the pharmaceutical composition of the present invention to promote catheter patency and/or enhance insulin absorption from the wound surrounding a catheter.

In certain embodiments, agents that increase blood flow through adipose tissue capillaries and venuoles may be included in the pharmaceutical composition. These agents include $\alpha_2$ and $\alpha_1$ receptor blockade agents such as Prazosin, Phenoxybenzamine, Phentolamine, Dibenamine, Tolazoline, Chlorpromazine, and Haloperidol. In an embodiment, agents that directly relax arteriolar and/or venous smooth muscle may be included. Such agents include, but are not limited to, Hydralazine with or without cutaneous blood flow, Adenosin, Dipyridamole, Diazoxide, Minoxidil, Papaverine, Nitroprusside, Prazosin, Histamine, Bradykinin, Nitroglycerine, Isosorbide Dinitrate, Amyl Nitrite, Erythrityl, and Tetranitrate. In an embodiment, a $B_2$ receptor agonist such as Isoproterenol, Dobutamine, Albuterol, Terbutaline, Aminophylline, Theophylline, or Caffeine may be included (singly or in combination). In an embodiment, a calcium channel inhibitor may be included. Such inhibitors include, but are not limited to, Amlodipine (Norvasc), Aranidipine (Sapresta), Azelnidipine (Calblock), Barnidipine (HypoCa), Benidipine (Coniel), Cilnidipine (Atelec, Cinalong, Siscard) Clevidipine (Cleviprex), Isradipine (DynaCirc, Prescal), Efonidipine (Landel), Felodipine (Plendil), Lacidipine (Motens, Lacipil), Lercanidipine (Zanidip), Manidipine (Calslot, Madipine), Nicardipine (Cardene, Carden SR), Nifedipine (Procardia, Adalat), Nilvadipine (Nivadil), Nimodipine (Nimotop), Nisoldipine (Baymycard, Sular, Syscor), Nitrendipine (Cardif, Nitrepin, Baylotensin), and Pranidipine (Acalas), singly or in combination. In an embodiment, an agent that blocks postganglionic adrenergic nerves (e.g., Guanethidine, Bretylium) may be included. In an embodiment, an agent that decreases oxygen, decreases pH, and increases carbon dioxide in local tissues may be included. It is believed that such agents may increase endothelium-derived nitric oxide, non-esterified fatty acids, prostaglandins and adenosine thus causing arteriolar dilation. In an embodiment, an agent that activates $\alpha_1$ and $B_1$ receptors on adipose cells may be included. In addition, the pharmaceutical composition of the invention may be administered in conjunction with, for example, approaches that increase cardiac output and total blood flow such as exercise, and in connection with local heating or other energy delivery designed to increase local blood flow.

In certain embodiments, agents that increase absorption through capillary and venuole walls into plasma may be included in the pharmaceutical composition. It is believed that these agents functions to enhance insulin uptake by capillaries, venuoles, and lymphatics. In an embodiment, agents that increase capillary and venuole permeability are included. Such agents include, for example, $H_1$ receptor agonists such as Histamine, 2-Methylhistamine, 2-(2-Pyridyl)ethylamine, and 2-(2-Thiazolyl)ethylamine and $H_2$ receptor agonists such as 4-Methylhistamine, Betazole, and Dimaprit, singly or in combination. In an embodiment, a higher insulin concentration may be employed to increase insulin concentration gradient from tissue to plasma. In a further embodiment, agents that increase hydrostatic pressure within tissue fluid may be used. Such agents include, for example, 3% Hypertonic saline, Histamine, Mannitol, Albumin, and Dextran. In another embodiment, agents that decrease osmotic pressure within tissue fluid may be used.

In certain embodiments, agents that increase active agent (e.g., insulin) diffusion may be included in the pharmaceutical composition. These agents can be used to minimize blood clot density, dissolve fibrin, DNA, and extracellular matrix connective tissue (collagen, elastin, hyaluronic acid) within granulation tissue while not affecting the biological activity of insulin. By way of non-limiting example, these agents include, Hyuronidase, Acetylcysteine, Streptokinase, Streptodornase, Urokinase, Recombinant Tissue Plasminogen Activator, Deoxyribonuclease, Chymotrypsin, Collagenase, Fibrinolysin, Deoxyribonuclease, Matrix Metalloproteinases, Heparin, and glucocorticoids such as Dexamethasone, Cortisol, Solumedrol, and Medrol, singly or in combination.

In certain embodiments, agents that increase the flow of active agent (e.g., insulin) into the lymphatic vessels may be included in the pharmaceutical composition. These agents increase the flow of active agent from the granulation tissue surrounding the infusion catheter to the lymphatic vessels. In an embodiment, agents that increase hydrostatic pressure within tissue fluid may be included. These agents include, for example, Histamine, 2-3% hypertonic saline, Urea, and Glucose. Other agents for rendering the formulation hypertonic include glycerin, dextrose, mannitol, NaCl, and KCl, as well as other mentioned perviously. In an embodiment, agents that increase water content within the tissue fluid may be included. These agents include, for example, water, histamine, and 2-3% hypertonic saline. In another embodiment, agents that increase lymph flow by increasing muscle movement and minute ventilation may be included.

In certain embodiments, agents that minimize active agent (e.g., insulin) degradation may be included in the pharmaceutical composition. Without wishing to be bound by theory, it is believed that such agents inhibit the activities of neutrophils, monocytes, macrophages, lymphocytes, and platelets which accumulate within the granulation tissue following tissue trauma and release proteases, lipases, oxygen radicals, IL-1, IL-6, IL-8, MCP-1, and TNF that degrade insulin surrounding the infusion catheter. These agents include, but are not limited to, glucocorticoids such as Dexamethasone, Cortisol, Solumedrol, and Medrol, anesthetic such as Lidocaine, Bupivicaine, Procaine, Etidocaine, Ropivican, Mepivican, Isoflurane, Halothane, Sevoflurane, Desflurane, and Enflurane, aprotinin or traysylol, aspirin and non-steroidal anti-inflammatory drugs (NSAIDs), cromolyn sodium, and immunosuppressant drugs such as Ciclosporin, Tacrolimus, and Sirolimus, singly or in combination.

In certain embodiments, agents that promote the wound healing process may be included in the pharmaceutical composition. In an embodiment, anti-inflammatory agents that inhibit, for example, the activities of eicosanoids may be included. These agents include, but are not limited to, aspirin and NSAIDs, anti-inflammatory cytokines, glucocorticoids, cyclosporines, Tacrolimus (Prograf), Sirolimus (rapamycin, Rapamune), Bradykinin, Adenosine, Nitric Oxide (NO), Matrix Metalloproteinases (MMPs), Exopeptidases (e.g., Aminopeptidase, Dipeptidase, Dipeptidyl peptidase, Tripeptidyl peptidase, Angiotensin-converting enzyme, Serine type carboxypeptidases: Cathepsin A, Metallocarboxypeptidases: Carboxypeptidase, Metalloexopeptidase) Endopeptidase (e.g., Serine proteases, Cysteine protease, Aspartic acid protease, Metalloendopeptidases, Secretase), and Deoxyribonucleases, singly or in combination.

In some aspects, the invention provides methods of treating or preventing a condition in a patient, by administering an active agent (e.g., insulin or other active agent) using an infusion set described herein. In some embodiments, the present invention provides methods for treating a subject with diabetes or other condition treated with rapid-acting insulins, using any of the pharmaceutical compositions or formulations including insulin or insulin analogues as described herein. The present invention also provides methods of treating a subject with diabetes using any of the insulin infusion sets for delivering rapid action insulin formulations as described herein. In an embodiment, the subject has type 1 diabetes and/or type 2 diabetes. In some embodiments, the patient exhibits insulin resistance. In a further embodiment, the subject has gestational diabetes. In certain embodiments, the subject is undergoing a regimen of basal insulin. The basal insulin may be administered from one to three times daily as a bolus injection, or is administered by continuous infusion. The continuous infusion may be of any of the pharmaceutical compositions or formulations including insulin or insulin analogues described herein, and it may utilize any of the infusion sets described herein.

Optionally, the subject may suffer from a metabolic disease for which insulin administration can be beneficial, such as obesity or metabolic syndrome. As used herein, the term "metabolic disease" refers to a group of identified disorders in which errors of metabolism, imbalances in metabolism, or sub-optimal metabolic homeostasis occur.

In an embodiment, the metabolic disease is obesity. For example, the subject may suffer from central obesity. In some embodiments, the obesity is one of simple obesity (alimentary obesity; usually resulting from consumption of more calories than the body can utilize), secondary obesity (usually resulting from an underlying medical condition, such as, for example, Cushing's syndrome and polycystic ovary syndrome), and childhood obesity. In some embodiments, the obesity is classified as: Class I, which includes a BMI between 30 and 34.99; Class II, which includes BMIs of 35 to 39.99; and Class III, which includes a BMI of over 40. Further, the present invention provides for obesity of any of classes I, II, or III that is further classified as severe, morbid, and super obesity.

In a further embodiment, the present invention provides methods of treating a subject who is prediabetic using any of the pharmaceutical compositions, formulations, or infusion sets including insulin as described herein. Prediabetes, also referred as impaired fasting glucose (IFG) or impaired glucose tolerance (IGT), is a precursor condition to type 2 diabetes. Prediabetes is diagnosed when fasting plasma glucose is between 100 to 125 mg/dL (5.56-6.94 mmol/L); or plasma glucose level is between 140 to 199 mg/dL (7.78-11.06 mmol/L) at 2-hours post-glucose load of 75 g; or an $A_1C$ level between 5.7 and 6.4%. Without intervention and appropriate treatment, people with prediabetes are at risk for developing type 2 diabetes.

In a further embodiment, the present invention provides a method of treating a subject with diabetes by administering one of the pharmaceutical compositions or formulations described herein through an infusion set, where the infusion set is replaced every 3rd day, or every 4th day, or every 5th day, or every 6th day, or every 7th day, or every 8th day, or every 9th day, or every 10th day, or every 11th day, or every 12th day, or every 13th day, or every 14th day, or every 15th day, or every 16th day, or every 17th day, or every 18th day, or every 19th day, or every 20th day, or every 21 day, or every 22 day, or every 23 day, or every 24th day, or every 25th day, or every 26th day, or every 27th day, or every 28th day, or every 29th day, or every 30th day, or every 31st day.

The pharmaceutical composition, formulation, and/or infusion set may be used to administer insulin before or during a meal. Due to the rapid absorption, the delivered insulin can shut off the conversion of glycogen to glucose in the liver, thereby preventing hyperglycemia. In an embodiment, the pharmaceutical composition, formulation, and/or infusion set are used to administer rapid action insulin at less than about 60 minutes, less than about 50 minutes, less than about 40 minutes, less than about 30 minutes, less than about 20 minutes, less than about 15 minutes, less than about 10 minutes, or less than about 5 minutes before a meal, or about the time of commencing a meal. In an embodiment, the pharmaceutical composition, formulation, and/or the infusion set are used for administering insulin within about 10 minutes to about 20 minutes of commencing a meal (e.g., before or after commencing a meal).

In various embodiments, the pharmaceutical composition or formulation is administered with or without an infusion set at least one time, at least two times, at least three times, at least four times, at least five times or more daily in connection with meals. In an embodiment, the pharmaceutical composition or formulation is administered (with or without an infusion set) at least three times daily in connection with meal consumption. In certain embodiments, the pharmaceutical composition or formulation is administered (or delivery is activated) upon symptoms of hyperglycemia.

In certain embodiments, the pharmaceutical composition or formulation is administered (with or without an infusion set) as a bolus subcutaneous injection. For example, administration may be achieved through a single bolus subcutaneous injection. In an embodiment, the pharmaceutical composition or formulation is administered through an infusion system, such as the infusion system as described herein for delivering rapid action insulin. In some embodiments, the pharmaceutical composition, formulation, and/or infusion set automatically administer rapid-acting insulin upon a detection of low blood glucose levels. The low blood glucose levels may be detected by a sensor proximal to or distant from an insulin infusion system such as the insulin infusion set as described herein.

In some embodiments, the volume of the pharmaceutical composition or formulation administered varies. In some embodiments, the volume of the rapid acting insulin composition delivered by the insulin infusion set varies. In various embodiments, the injectate volume is less than about 2 ml, less than about 1.9 ml, less than about 1.8 ml, less than about 1.7 ml, less than about 1.6 ml, less than about 1.5 ml, less than about 1.4 ml, less than about 1.3 ml, less than about 1.2 ml, less than about 1.1 ml, less than about 1.0 ml, less than about 0.9 ml, less than about 0.8 ml, less than about 0.7 ml, less than about 0.6 ml, less than about 0.5 ml, less than about 0.4 ml, less than about 0.3 ml, less than about 0.2 ml, or less than about 0.1 ml, or less than about 90 µl, or less than about 80 µl, or less than about 70 µl, or less than about 60 µl, or less than about 50 µl, or less than about 40 µl, or less than 30 µl, or less than about 20 µl, or less than about 10 µl, or less than about 9 µl, or less than about 8 µl, or less than about 7 µl, or less than about 6 µl, or less than about 5 µl, or less than about 4 µl, or less than about 3 µl, or less than about 2 µl, or less than about 1 µl, or less than about 0.5 µl, or less than about 0.1 µl, inclusive of all values and ranges therebetween.

Administration of the pharmaceutical composition or formulation may be accompanied by the use of one or more of low intensity ultrasound (LITUS), mechanical massage, and electrophoresis. A combination of these applications is believed to provide synergistic effects in, for example, enhancing the speed of insulin absorption into the circulation and/or promoting a more rapid insulin pharmacokinetics. In an embodiment, the ultrasound, mechanical message, and/or electrophoresis are applied for at least about 4 hours, at least about 3 hours, at least about 2 hours, at least about 1.5 hours, at least about 60 minutes, at least about 50 minutes, at least about 40 minutes, at least about 30 minutes, at least about 20 minutes, at least about 10 minutes, or at least about 5 minutes after bolus infusion. In an embodiment, the ultrasound, mechanical message, and/or electrophoresis are applied for at least about 60 minutes after bolus infusion. In another embodiment, the ultrasound, mechanical message, and/or electrophoresis are applied for at least about 30 minutes before and/or after bolus infusion. In a further embodiment, the ultrasound, mechanical message, and/or electrophoresis are applied about 10 minutes before and/or after bolus infusion. The ultrasound, mechanical message, and/or electrophoresis may automatically operate for a predetermined amount of time. Alternatively, the ultrasound, mechanical massage, or electrophoresis may be turned off based on an algorithm, which may optionally trace blood glucose levels as an input. Alternatively, the ultrasound, mechanical message, and/or electrophoresis may be turned off manually by the subject.

In an embodiment, the infusion set may be placed on the epidermis and be replaced about every: ¼ day, ½ day, ¾ day, 1 day, 1.5 days, 2 days, 2.5 days, 3 days, 3.5 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days.

In an embodiment, the subject may receive the pharmaceutical composition or formulation with or without a basal insulin composition as controlled by an artificial pancreas system, which may further comprise a glucose sensor. For example, the subject may receive the rapid acting insulin composition delivered by the infusion set upon detection of hyperglycemia by the glucose sensor, and the subject may also receive periodic administrations (e.g., 1 to 3 times daily) of a long-acting basal insulin composition, all controlled by the artificial pancreas system.

Where a basal insulin is delivered, in some embodiments the basal insulin is infused at a daily dose of about 10 U to about 500 U of insulin, such as about 10 U to about 100 U of insulin.

The present invention is further illustrated by the following non-limiting examples.

EXAMPLES

Example 1

Euglycemic Clamp Studies Using Insulin Formulations with a Calcium Ion Chelator

Euglycemic clamp studies were conducted on Yorkshire pigs to study the pharmacodynamics (PD) of insulin absorption. On the day of study, each animal underwent anesthesia with isoflurane and was endotracheally intubated. Oxygen saturation and end-tidal expired $CO_2$ were continuously monitored. To block endogenous pancreatic α- and β-cell secretion, pigs were given i.v. octreotide acetate before beginning the clamp and continuously thereafter. IV catheters were placed and baseline euglycemia established with 10% dextrose infusion.

A s.q. injection of the test formulation was given in the nape of the neck: skin was pinched and the needle inserted 0.8 mm before the injection was made.

A variable-rate glucose infusion (GIR) was given to maintain blood glucose (BG) at approximately 85 mg/dl for 3-4 hours until the GIR returned to pre-insulin baseline. A computerized protocol for glucose clamping was used. 2-ml blood samples for insulin assay were obtained according to the following schedule: from 0-40 min after insulin delivery, 5-minute intervals; from 50-140 min, 10-minute intervals; and from 160 min—to the point when GIR was back to baseline, 20-min intervals.

For each of the analyses, the fitted curve, not the raw data, was used. GIR was graphed, and curve parameters calculated: time to half-maximal effect (early), time to half-maximal effect (late), time to maximal effect, and area-under-the-curve (AUC) over baseline.

Figure 4:
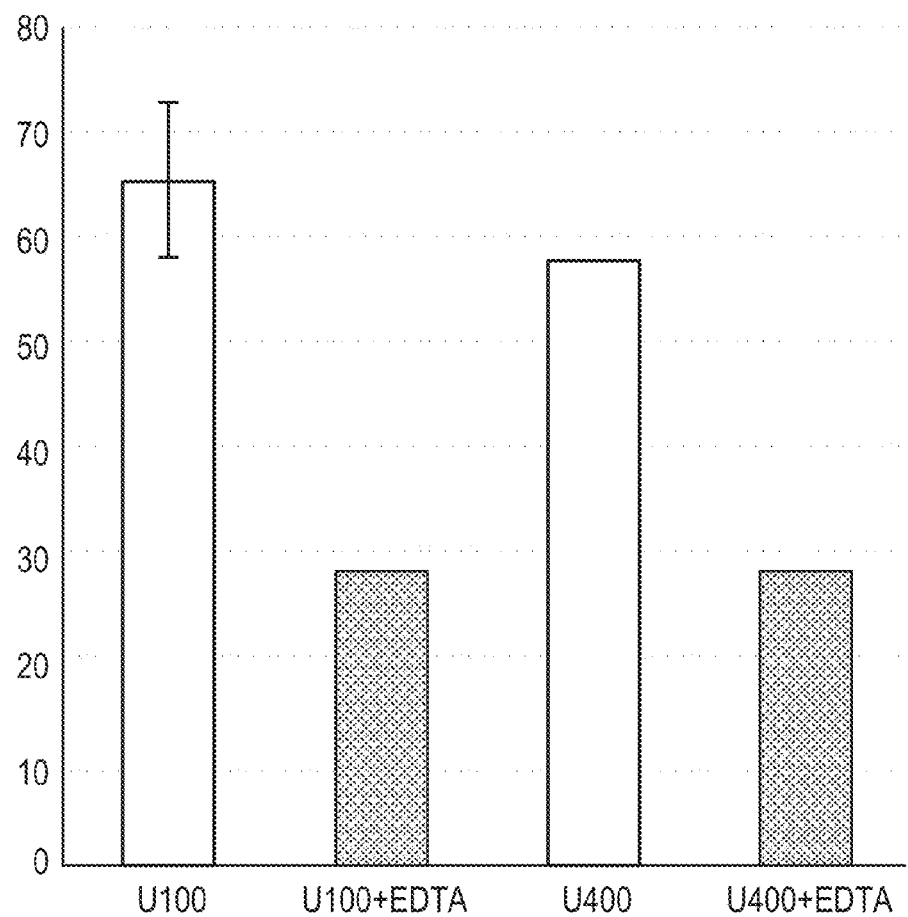
FIG. 4 shows the rate of onset of insulin action from euglycemic clamp studies in Yorkshire swine. Onset of insulin action is measured in this example as time to ½ maximum potency. Studies use a monomeric insulin (Fluorolog). Studies with and without EDTA are shown.

Formulations of Fluorolog (Asp B10, orthomonofluorophenylalanine-B24, lispro insulin) in a zinc free phosphate buffer (which is an insulin analog that is stable in a zinc-free formulation) was administered at U100 (N=4) and U400 (N=2) concentrations with (N=2) and without (N=4) 5 mM EDTA. The onset of insulin action (determined as the time until the GIR was half way to its peak) was twice as fast in the formations containing EDTA as in those that did not. FIG. 4.

Example 2

Euglycemic Clamp Studies Using Energy Delivery

Euglycemic clamp studies were conducted on Sinclair pigs to study the pharmacokinetics (PK) and pharmacodynamics (PD) of insulin absorption. On the day of study each animal underwent anesthesia with isoflurane and was endotracheally intubated. Oxygen saturation and end-tidal expired $CO_2$ were continuously monitored. To block endogenous pancreatic α- and β-cell secretion, pigs was given i.v. octreotide acetate before beginning the clamp and continuously thereafter. IV catheters were placed and baseline euglycemia established with 10% dextrose infusion.

Figure 5:
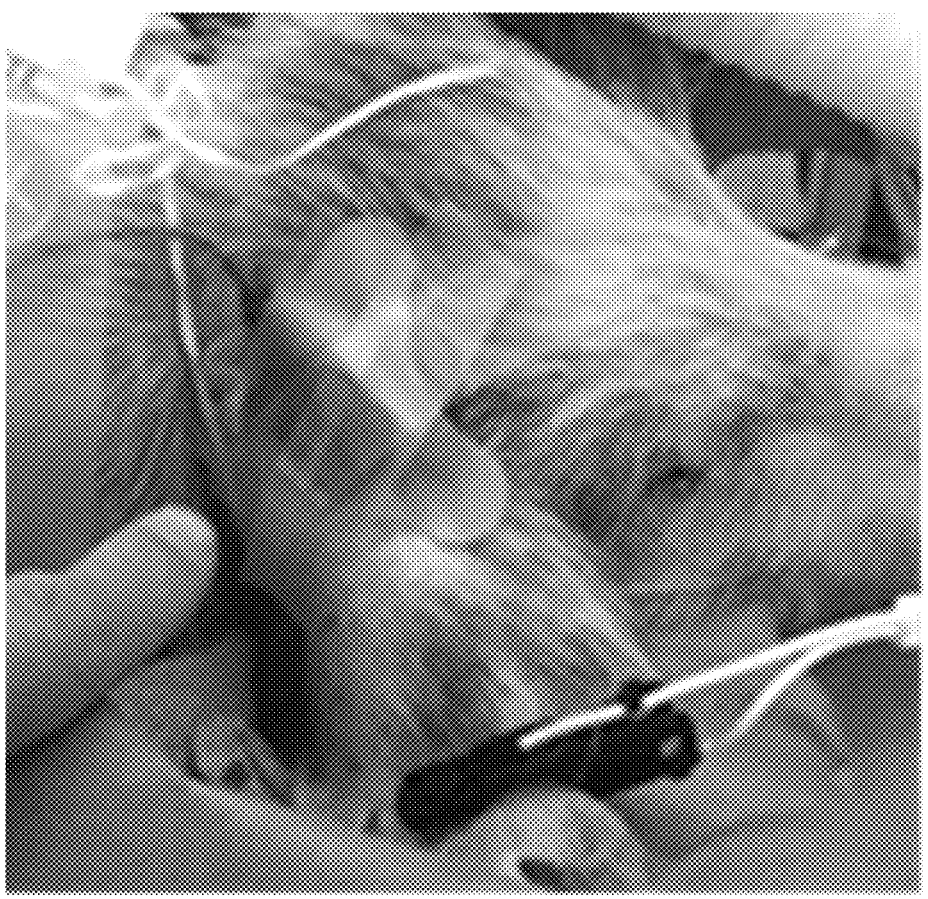
FIG. 5 shows an UltrOZ device applied to a shaved injection site on a Sinclair pig.

A ZetrOZ UltrOZ low intensity ultrasound (LITUS) therapy device was turned on and placed over the injection site for 30 minutes prior to injection (FIG. 5). The UltrOZ device is about 4 cm in diameter, designed for veterinary use, and delivers LITUS at 3 MHz at an energy concentration of about 50 mW/cm2 near the injection site. A s.q. injection of humalog was given in the nape of the neck: skin was pinched and the needle inserted 0.8 mm before the injection is made. The device was replaced after the injection and left in place for the remainder of the procedure. To verify that this exposure to LITUS does not contribute to insulin degradation, a sample of Humalog was exposed to this intensity of LITUS for 48 hours at 37° C., after which no evidence of chemical degradation by HPLC or visual fibril formation was detected.

A variable-rate glucose infusion (GIR) was given to maintain BG at approximately 85 mg/dl for 3-4 hr until the GIR returned to pre-insulin baseline. The computerized protocol for glucose clamping was used. 2-ml blood samples for insulin assay were obtained according to the following schedule: from 0-40 min after insulin delivery, 5-minute intervals; from 50-140 min, 10-minute intervals; and from 160 min—to the point when GIR was back to baseline, 20-min intervals.

For each of these analyses, the fitted curve, not the raw data, was used. GIR was graphed, and curve parameters calculated: time to half-maximal effect (early), time to half-maximal effect (late), time to maximal effect, and area-under-the-curve (AUC) over baseline.

Figure 6:
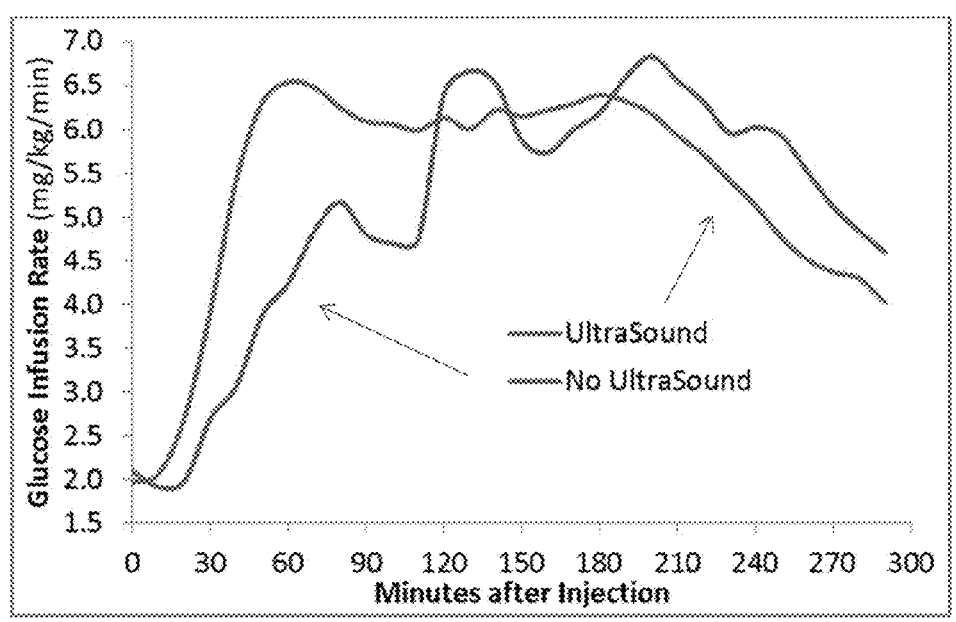
FIG. 6 shows the result of euglycemic clamp studies of subcutaneous lispro insulin injection in a single Sinclair pig, which demonstrates: faster onset, a longer plateau, and essentially identical potency (AUC) for injection exposed to ultrasound.

These studies showed that a more rapid PK and more rapid onset of PD (FIG. 6) were achieved when the injection site was exposed to ultrasound.

Example 3

Insulin Movement in an Electrical Field

To assess the effect of using electrophoresis to accelerate the diffusion of s.q. administered insulin in a target direction through a hydrogel medium like those found in the septae of the s.q. tissue, the rate movement of various insulin analogs were tested in an acrylamide gel under 0.5 mA/cm current for 15 minutes, which is standard for commercial iontophoresis devices. Insulin analogs with a variety of net charges were tested. In addition to Humalog®, we also tested Asp-B10 ortho-monofluorophenylalanine-B24, lispro insulin (Fluorolog), Glu-B31 Glu-B32 insulin (Hexalog-1) and Glu-A8 Glu-B31 Glu-B32 insulin (Hexalog-2), which are significantly more negatively charged than human insulin. The results (Table 3) suggest that insulin is highly mobile under a physiologically tolerable electric field and that more negatively charged insulin analogs are even more mobile.

TABLE 3

Migration in acrylamide gel at pH 7 of insulin analogs under 0.5 mA/cm for 15 min

| Insulin Analog | Charge | Distance (cm) | % of Lispro |
|---|---|---|---|
| Lispro | −2 | 1.5 | 100 |
| Fluorolog | −3.3 | 1.8 | 120 |
| Hexalog-1 | −4 | 2.2 | 146 |
| Hexalog-2 | −5 | 2.6 | 173 |

Example 4

Insulin Movement in Tissue

Figure 12A:
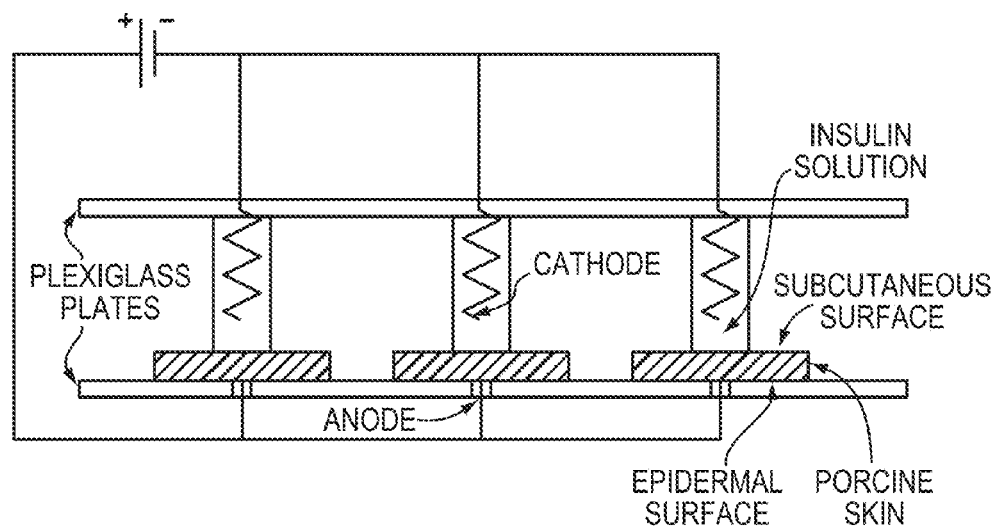
FIGS. 12A and 12B show a diagram of the Franz apparatus used to demonstrate insulin migration in tissue (12A) and the actual implementation of that apparatus (12B).
Figure 12B:
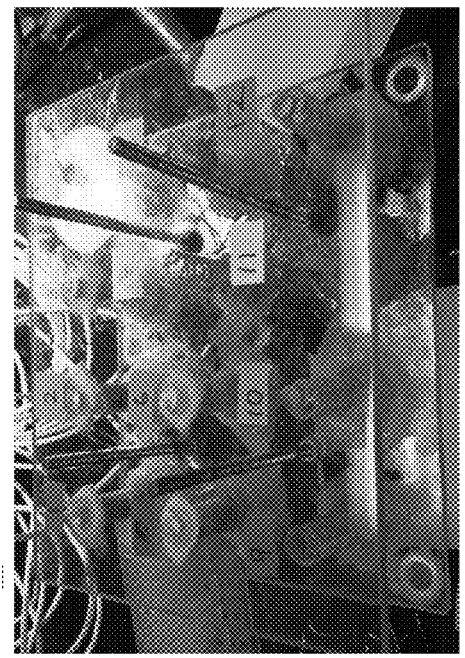

The effect of an electric field was explored on migration through the subcutis using fresh porcine abdominal skin tissue obtained from local abattoirs. To do this, a modified Franz apparatus was developed that could test up to 12 samples simultaneously (FIGS. 12A, 12B). Full-thickness porcine skin tissue plugs that were three cm in diameter were placed subcutis-down in individual wells over reservoirs containing cathodes below 2 ml of test solution. The device was then inverted to run the experiments.

Tissue and test solution were maintained at 37° C. using a heat lamp and monitored with a digital thermometer probe placed between the plexiglass plates, adjacent to the tissues. Anodes were inserted into conductive paste placed on the epidermal surface. Utilizing multiple electrophoresis power sources, 10V or 20V of electromotive potential was then run across each cathode-anode pair for one hour. Current typically started at approximately 20 mA typically fell over time to about 5 mA likely due to ion depletion. Current tended to be higher in wells receiving 20 volts vs. those receiving 10 V. We settled on NiChrome (80/20 Nickel/Chromium) electrodes, which were stable and produced only minor and occasional discoloration.

Figure 13:
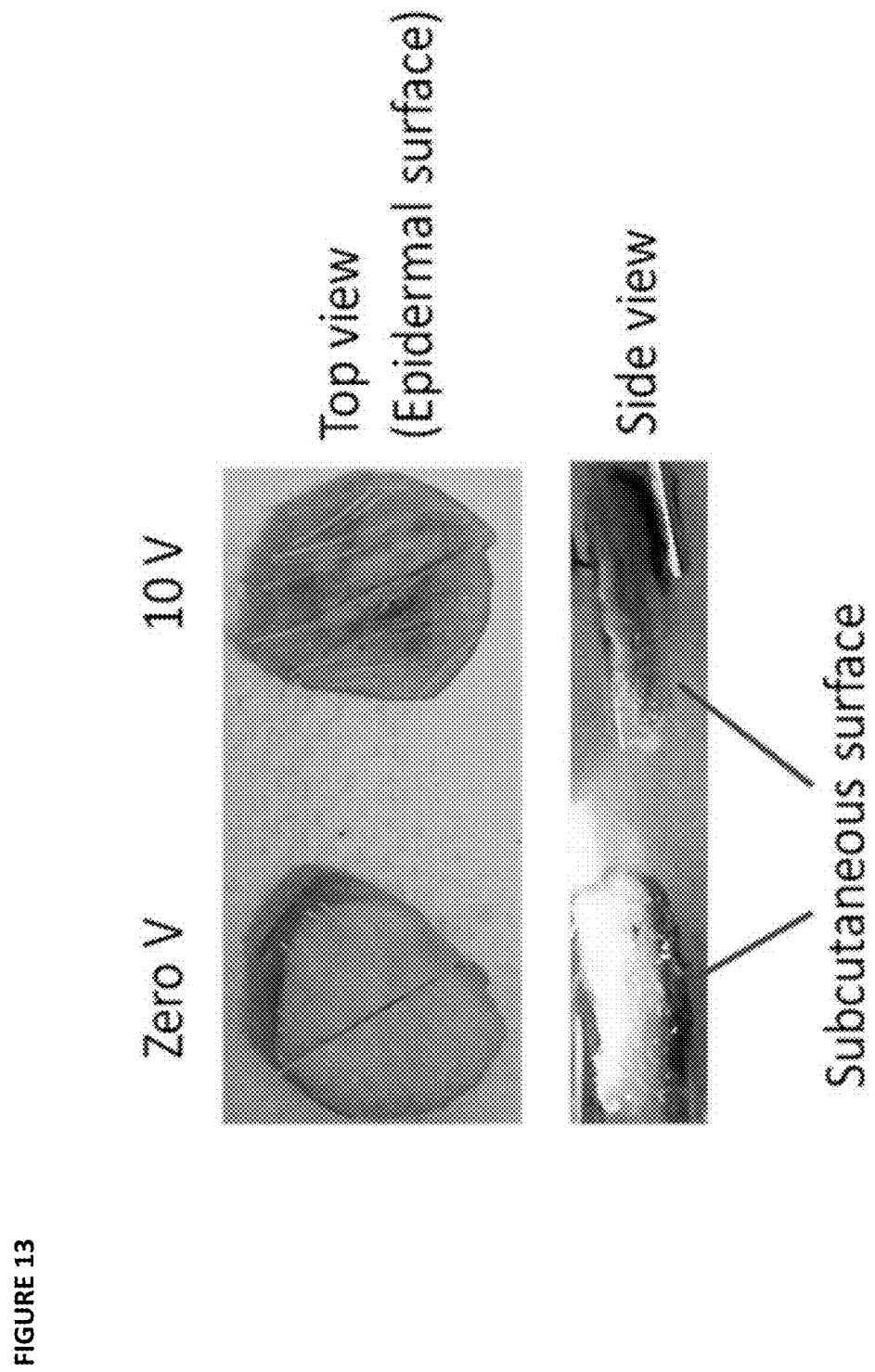
FIG. 13 shows Porcine skin following treatment with bromophenol blue (0.05%, pH7.3) without (zero V) and with (10 V) EMF through the full thickness skin layers at 37° C. for one hour. The negatively charged bromophenol blue penetrated the tissue under the influence of the EMF.

We tested the apparatus using a solution of bromophenol blue (BPB), a 0.67 kDa dye that appears blue above pH 4.6 and carries a negative charge near neutral pH similar to that of insulin. We were able to demonstrate significant migration of the dye when the voltage was on vs. when it was off (FIG. 13). The epidermal surface was dark blue in voltage-treated tissue. An edge view showed that dye penetrated through the subcutis in voltage-treated tissue (but not in 0 V). This demonstrates migration of charged chemicals through subcutaneous tissue.

We next conducted pilot experiments using Cyanine-5-labeled insulin (Cy5-insulin, P/N IS1-S5-1, Nanocs, Inc.): human insulin conjugated to cyanine-5-NHS-ester, a fluorophore with MW of 619 Da that excites optimally at 647 nm and emits with peak energy at 662 nm. Each insulin molecule in Cy5-insulin is labeled with 2-7 fluorophore units according to the manufacturer. Assuming a normal distribution of fluorophore labeling efficiency, about 2% of the insulin molecules will have 1 functional fluorophore unit. Cy5 at neutral pH has a net +1 charge and insulin has a net −2 charge at neutral pH, so the average overall charge of the single-labeled Cy5-insulin should be negative, resulting in migration to the anode.

Figure 14:
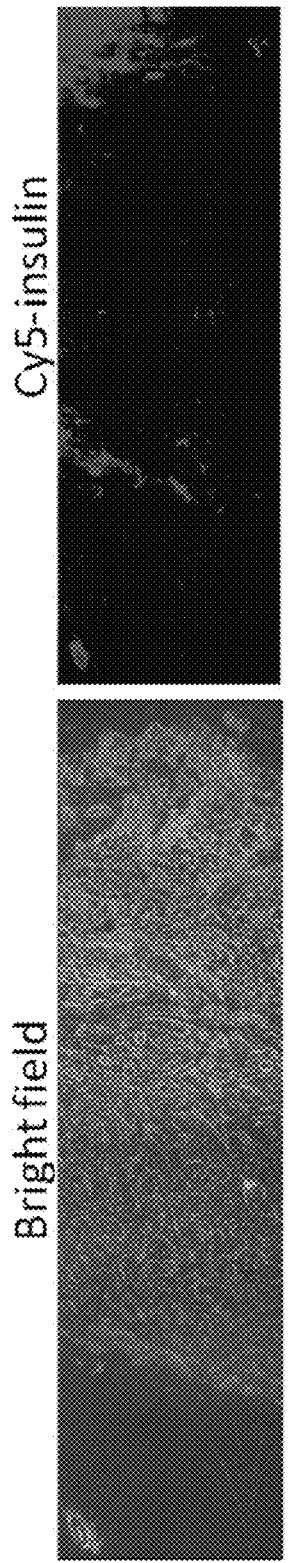
FIG. 14 shows the localization of Cy5-insulin in pig skin after 1 hour of electrophoresis under an EMF of 10 V. Epidermis is to the left.
Figure 15:
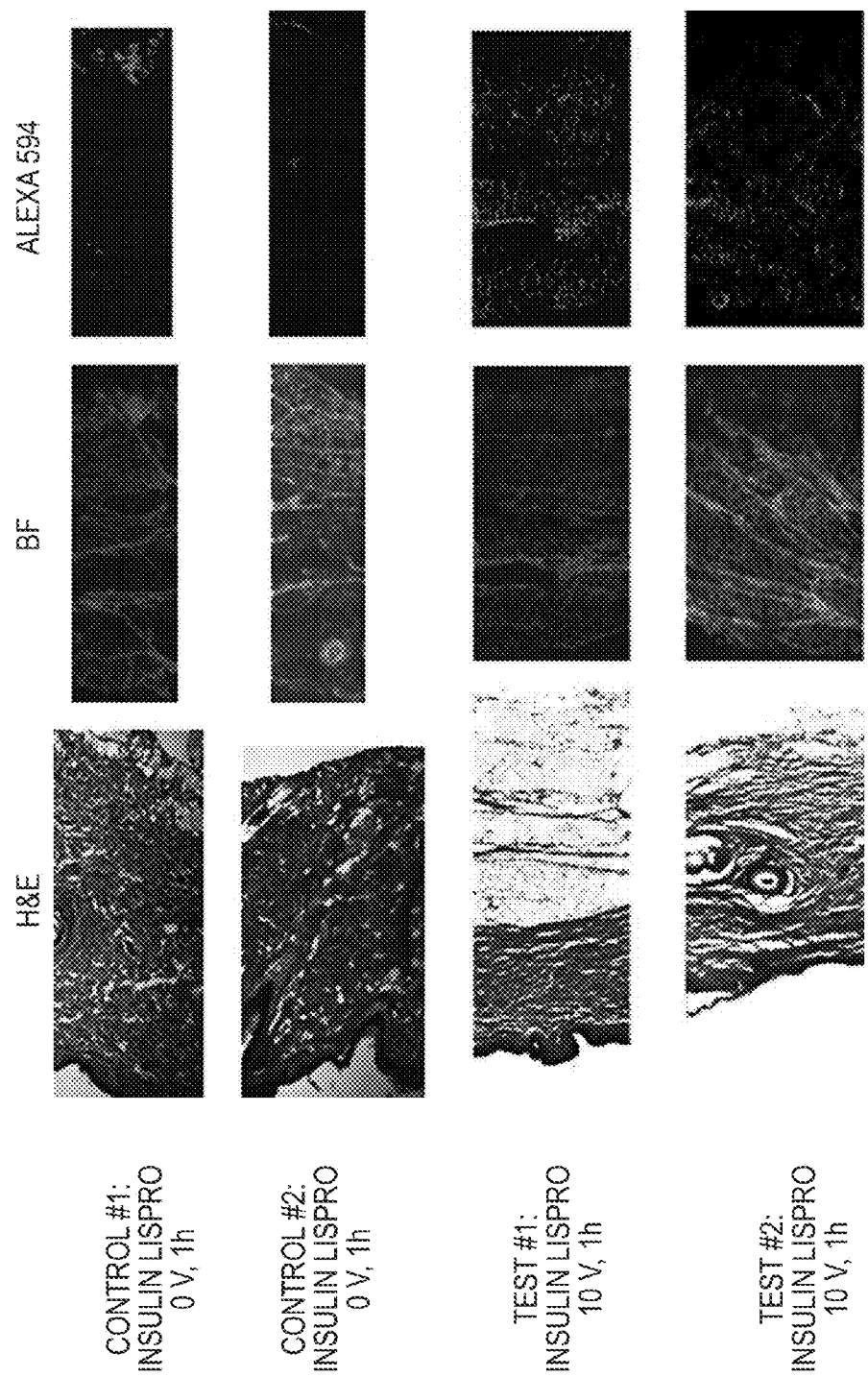
FIG. 15 shows two representative control samples (no voltage applied) and two test skin samples (10 volts applied) exposed to LisPro insulin on the subcutaneous surface during a one-hour treatment period. All skin samples were from the same animal and are oriented with the epidermis on the left and the subcutis on the right. The left column images are skin thin sections stained with H&E. The middle column depicts the bright-field (BF) images that correspond to the Alexa 594 images (right column). In tissues where no voltage was applied, the Alexa 594 label is visible only at the subcutaneous surface (Control #1) or is undetectable in any skin layer (Control #2). By comparison, the Alexa 594 images from test samples 1 and 2 indicate fluorescence label through all layers of skin, with concentration (Test #1) at the hypodermal boundary, indicating detectable insulin movement from the subcutaneous surface into the deeper skin layers.

FIG. 14 shows the Cy5-insulin distribution in a thin section exposed to Cy5-insulin (0.62 U insulin/ml) during an applied 10-volt differential for 2 hours. Following one hour of electrophoresis, the tissues were removed, bisected through the center of the skin disk in a plane perpendicular to the epidermal surface, placed in 4% paraformaldehyde (pH 7.4) for 18-24 hrs and subsequently transferred to 30% sucrose until embedded in OCT. From each frozen OCT block, 14-μm sections were cut, mounted on microscope slides and imaged through a 10× objective on a Nikon deconvolution brightfield-epifluorescence microscope fitted with a cube filter appropriate for Cy5 absorption and emission spectra and a charge-coupled device (CCD) digital camera. The bright-field (BF) image shows the full skin thickness with epidermis on the left and subcutis on the right. Cy5 label can be seen to exist predominantly in the subcutis, but has also penetrated to the dermis and epidermis, indicating migration of the fluorescence-tagged insulin through the full skin thickness We then conducted experiments using unlabeled insulin lispro. Migration of unlabeled insulin lispro was detected by immunohistochemistry (IHC) and processed according to a protocol similar to that described above for the Cy5-insulin experiment. One microscope slide was stained with H&E; an adjacent slide was stained with a Guinea pig polyclonal antibody (Ab) (Abcam ab7842), which was detected by a goat anti-Guinea pig polyclonal IgG H&L (Alexa Fluor® 594; Abcam ab150188). Microscopic images from this experiment are shown in FIG. 15 and demonstrate insulin migration though tissue under the influence of an electric field.

Example 5

Enhanced Insulin Absorption Through Formulation

In five studies in Yucatan swine, various formulations of insulin analogue T-0339 were injected subcutaneously and the effect of insulin action were monitored by the glucose infusion rate required to maintain euglycemia. T-0339 has an A chain with the amino acid sequence: GIVEQCCESIC-SLYQLENYCN (SEQ ID NO: 20), and a B chain with the amino acid sequence: FVNQHLCGSDLVEALYL-VCGERGXFYTPET (SEQ ID NO: 21), where X is ortho-monofluorophenylalanine. T-0339 has three disulfide linkages which are identical to human insulin, i.e., two inter-chain disulfide bonds connecting A7 to B7 and A20 to B19 and one intra-chain disulfide bond connecting A6 to A11.

T-0339 is negatively charged (−3) and when formulated in a Tris buffer took 90 minutes to reach half-peak potency. However, when excess molar quantities of EDTA (20 mM), Citrate (20 mM), and EDTA (10 mM)+Citrate (8.6 mM) were added to the formulation, the time to half-peak potency was reduced significantly. EDTA and Citrate are both negatively charged ions (−4 and −3 respectively) and it is hypothesized that these molecules take the place of insulin in positively charged electrostatic binding sites in the subcutaneous tissue, allowing the monomeric insulin to move more freely to the vessels for rapid absorption. The combined effect of EDTA and citrate was not synergistic in this study. See FIG. 16. Formulations consisted of 50 mM Tris, 3.2 mg/ml m-cresol and glycerin adjusted to maintain equivalent tonicity (0.8-0.9% NaCl equivalent).

FIGS. 17 to 19 show additional studies: FIG. 17 shows $T_{max}$ ½ early; FIG. 18 shows AUC ½ late, and FIG. 19 shows $T_{max}$ ½ late. Excipients include EDTA, citrate, and sodium benzoate.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

What is claimed is:

1. A pharmaceutical composition formulated for subcutaneous or intra-dermal administration comprising an aqueous formulation of:
   (i) an insulin analogue that is predominately in monomeric and/or dimeric form at a concentration of at least 100 insulin units per mL (100 IU);
   (ii) one or more calcium ion-chelating agents and one or more additional excipients; and
   wherein the composition comprises less than 0.05 moles of zinc per mole of insulin analogue.

2. The pharmaceutical composition of claim 1, wherein the calcium ion-chelating agent comprises one or more amino polycarboxylic acid compounds.

3. The pharmaceutical composition of claim 2, wherein the calcium ion-chelating agent comprises one or more of ethylenediamine tetraacetic acid (EDTA), ethylene glycol tetraacetic acid (EGTA), and cyclohexane diamino tetraacetic acid (CDTA), and wherein the agent is optionally a sodium or magnesium salt.

4. The pharmaceutical composition of claim 1, wherein the calcium ion-chelating agent comprises an anionic polysaccharide.

5. The pharmaceutical composition of claim 4, wherein the calcium ion-chelating agent comprises alginic acid.

6. The pharmaceutical composition of claim 1, wherein the calcium ion-chelating agent comprises one or more organosulfur compounds.

7. The pharmaceutical composition of claim 6, wherein the calcium ion-chelating agent comprises alpha lipoic acid.

8. The pharmaceutical composition of claim 1, wherein the calcium ion-chelating agent comprises one or more di- or tri-carboxylic acids.

9. The pharmaceutical composition of claim 8, wherein the calcium ion-chelating agent comprises citric acid or oxalic acid.

10. The pharmaceutical composition of claim 1, wherein the calcium ion-chelating agent(s) comprise one or more of penicillamine, and extract or partial extract of chlorella and/or cilantro.

11. The pharmaceutical composition of claim 1, wherein the composition provides an onset of insulin activity of less than about 40 minutes after subcutaneous administration.

12. The pharmaceutical composition of claim 11, wherein the composition provides a duration of insulin activity of from 1 to 2 hours.

13. The pharmaceutical composition of claim 1, wherein the composition is stable for at least about one month at 25° C.

14. The pharmaceutical composition of claim 13, wherein the monomeric insulin analogue has one or more mutations that reduce or eliminate fibril formation.

15. The pharmaceutical composition of claim 14, wherein the monomeric insulin analogue comprises one or more mutations at positions corresponding to the following positions of native human insulin: B2, B3, B4, B10, B13, B17, B28, B29, A8, A10, A12, A13, A14, A17, and A21, and is optionally a single chain insulin.

16. The pharmaceutical composition of claim 15, wherein the monomeric insulin analogue contains one or more of:
Leu at the position corresponding to A3;
Glu, His, Gln at the position corresponding to A8;
Cys at the position corresponding to A10;
Asp or Thr at the position corresponding to A12;
Trp, Tyr, His, Glu, Ala, or Phe at the position corresponding to A13;
His or Glu at the position corresponding to A14;
Trp, Tyr, Ala, His, Glu, Gln, Phe, or Apn, at the position corresponding to A17
Gly at the position corresponding to A21;
Cys at the position corresponding to B2;
Lys at the position corresponding to B3;
Cys at the position corresponding to B4;
Asp at the position corresponding to B10;
Trp, Tyr, Ala, His, Glu, Phe, Apn, or Gln at the position corresponding to B13;
Trp, Tyr, His, or Gln at the position corresponding to B17;
Trp, Tyr, His, Gln, Asp, Thr, Ala, Phe, or Cha at the position corresponding to B24; and
Glu at the position corresponding to B29.

17. The pharmaceutical composition of claim 13, wherein the monomeric insulin analogue has a deletion of amino acids B1-B3.

18. The pharmaceutical composition of claim 1, wherein the monomeric insulin analogue is a single chain insulin analogue having a peptide linker between the A and B chains.

19. The pharmaceutical composition of claim 1, wherein the composition comprises one or more pharmaceutically acceptable excipients.

20. The pharmaceutical composition of claim 19, wherein the composition comprises one or more of a pharmaceutically acceptable buffer, stabilizing agent(s), surfactant(s), solubilizing agent, anti-aggregation agent, diffusion-enhancing agent, absorption enhancing agent, and preservative(s).

21. The pharmaceutical composition of claim 1, wherein the composition is provided within an insulin infusion set.

22. A method for treating a subject with diabetes mellitus, comprising: administering the pharmaceutical composition of claim 1 to said subject.

23. The method of claim 1, wherein the additional excipient comprises arginine.

24. The pharmaceutical composition of claim 1, wherein the composition comprises EDTA or EGTA as the calcium ion-chelating agent at from 5 to 25 mM.

25. The pharmaceutical composition of claim 1, further comprising isosorbide mononitrate.

26. The pharmaceutical composition of claim 1, further comprising Lidocaine.

27. The pharmaceutical composition of claim 1, further comprising a surfactant.

* * * * *

UNITED STATES PATENT AND TRADEMARK OFFICE
CERTIFICATE OF CORRECTION

PATENT NO. : 9,901,622 B2
APPLICATION NO. : 15/110758
DATED : February 27, 2018
INVENTOR(S) : Jeffrey I. Joseph et al.

It is certified that error appears in the above-identified patent and that said Letters Patent is hereby corrected as shown below:

On the Title Page

Item (73) Assignee:
Change "THERMALIN DIABETES, INC.," to -- THERMALIN INC. --

Signed and Sealed this
Fifth Day of March, 2019

Andrei Iancu
*Director of the United States Patent and Trademark Office*

SEQUENCE LISTING

```
<160> NUMBER OF SEQ ID NOS: 21

<210> SEQ ID NO 1
<211> LENGTH: 5
<212> TYPE: PRT
<213> ORGANISM: Artificial sequence
<220> FEATURE:
<223> OTHER INFORMATION: Synthetic sequence

<400> SEQUENCE: 1

Lys Pro Ile Glu Glu
1               5
```

```
<210> SEQ ID NO 2
<211> LENGTH: 5
<212> TYPE: PRT
<213> ORGANISM: Artificial sequence
<220> FEATURE:
<223> OTHER INFORMATION: Synthetic sequence

<400> SEQUENCE: 2

Glu Pro Ile Glu Glu
1               5

<210> SEQ ID NO 3
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (2)..(2)
<223> OTHER INFORMATION: X is ornithine

<400> SEQUENCE: 3

Pro Xaa Thr Glu Glu
1               5

<210> SEQ ID NO 4
<211> LENGTH: 4
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (2)..(2)
<223> OTHER INFORMATION: X is ornithine
<220> FEATURE:
<221> NAME/KEY: MISC_FEATURE
<222> LOCATION: (4)..(4)
<223> OTHER INFORMATION: X is ornithine

<400> SEQUENCE: 4

Pro Xaa Thr Xaa
1

<210> SEQ ID NO 5
<211> LENGTH: 4
<212> TYPE: PRT
<213> ORGANISM: Artificial sequence
<220> FEATURE:
<223> OTHER INFORMATION: Synthetic sequence

<400> SEQUENCE: 5

Gly Pro Arg Arg
1

<210> SEQ ID NO 6
<211> LENGTH: 6
<212> TYPE: PRT
<213> ORGANISM: Artificial sequence
<220> FEATURE:
<223> OTHER INFORMATION: Synthetic sequence

<400> SEQUENCE: 6

Gly Gly Gly Pro Arg Arg
1               5

<210> SEQ ID NO 7
<211> LENGTH: 5
```

```
<212> TYPE: PRT
<213> ORGANISM: Artificial sequence
<220> FEATURE:
<223> OTHER INFORMATION: Synthetic sequence

<400> SEQUENCE: 7

Gly Gly Pro Arg Arg
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic sequence

<400> SEQUENCE: 8

Gly Ser Glu Gln Arg Arg
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic sequence

<400> SEQUENCE: 9

Arg Arg Glu Gln Lys Arg
1               5

<210> SEQ ID NO 10
<211> LENGTH: 8
<212> TYPE: PRT
<213> ORGANISM: Artificial sequence
<220> FEATURE:
<223> OTHER INFORMATION: Synthetic sequence

<400> SEQUENCE: 10

Arg Arg Glu Ala Leu Gln Lys Arg
1               5

<210> SEQ ID NO 11
<211> LENGTH: 6
<212> TYPE: PRT
<213> ORGANISM: Artificial sequence
<220> FEATURE:
<223> OTHER INFORMATION: Synthetic sequence

<400> SEQUENCE: 11

Gly Ala Gly Pro Arg Arg
1               5

<210> SEQ ID NO 12
<211> LENGTH: 7
<212> TYPE: PRT
<213> ORGANISM: Artificial sequence
<220> FEATURE:
<223> OTHER INFORMATION: Synthetic sequence

<400> SEQUENCE: 12

Gly Gly Gly Pro Gly Lys Arg
1               5

<210> SEQ ID NO 13
<211> LENGTH: 8
<212> TYPE: PRT
```

-continued

```
<213> ORGANISM: Artificial sequence
<220> FEATURE:
<223> OTHER INFORMATION: Synthetic sequence

<400> SEQUENCE: 13

Glu Glu Gly Ser Arg Arg Ser Arg
1               5

<210> SEQ ID NO 14
<211> LENGTH: 6
<212> TYPE: PRT
<213> ORGANISM: Artificial sequence
<220> FEATURE:
<223> OTHER INFORMATION: Synthetic sequence

<400> SEQUENCE: 14

Glu Glu Gly Pro Arg Arg
1               5

<210> SEQ ID NO 15
<211> LENGTH: 6
<212> TYPE: PRT
<213> ORGANISM: Artificial sequence
<220> FEATURE:
<223> OTHER INFORMATION: Synthetic sequence

<400> SEQUENCE: 15

Gly Glu Gly Pro Arg Arg
1               5

<210> SEQ ID NO 16
<211> LENGTH: 8
<212> TYPE: PRT
<213> ORGANISM: Artificial sequence
<220> FEATURE:
<223> OTHER INFORMATION: Synthetic sequence

<400> SEQUENCE: 16

Ala Glu Gly Ser Arg Arg Ser Arg
1               5

<210> SEQ ID NO 17
<211> LENGTH: 8
<212> TYPE: PRT
<213> ORGANISM: Artificial sequence
<220> FEATURE:
<223> OTHER INFORMATION: Synthetic sequence

<400> SEQUENCE: 17

Ala Ser Gly Ser Arg Arg Ser Arg
1               5

<210> SEQ ID NO 18
<211> LENGTH: 7
<212> TYPE: PRT
<213> ORGANISM: Artificial sequence
<220> FEATURE:
<223> OTHER INFORMATION: Synthetic sequence

<400> SEQUENCE: 18

Glu Glu Gly Ser Arg Arg Asp
1               5

<210> SEQ ID NO 19
<211> LENGTH: 7
<212> TYPE: PRT
<213> ORGANISM: Artificial sequence
```

```
<220> FEATURE:
<223> OTHER INFORMATION: Synthetic sequence

<400> SEQUENCE: 19

Glu Glu Gly Ser Arg Arg Lys
1               5

<210> SEQ ID NO 20
<211> LENGTH: 21
<212> TYPE: PRT
<213> ORGANISM: Artificial sequence
<220> FEATURE:
<223> OTHER INFORMATION: Synthetic sequence

<400> SEQUENCE: 20

Gly Ile Val Glu Gln Cys Cys Glu Ser Ile Cys Ser Leu Tyr Gln Leu
1               5                   10                  15

Glu Asn Tyr Cys Asn
            20

<210> SEQ ID NO 21
<211> LENGTH: 30
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (24)..(24)
<223> OTHER INFORMATION: X is ortho-monofluorophenylalanine

<400> SEQUENCE: 21

Phe Val Asn Gln His Leu Cys Gly Ser Asp Leu Val Glu Ala Leu Tyr
1               5                   10                  15

Leu Val Cys Gly Glu Arg Gly Xaa Phe Tyr Thr Pro Glu Thr
            20                  25                  30
```